United States Patent
Yeung et al.

(10) Patent No.: US 8,354,410 B2
(45) Date of Patent: Jan. 15, 2013

(54) COMPOUNDS FOR THE TREATMENT OF HEPATITIS C

(75) Inventors: Kap-Sun Yeung, Madison, CT (US); Katharine A. Grant-Young, Madison, CT (US); John F. Kadow, Wallingford, CT (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 62 days.

(21) Appl. No.: 13/043,747

(22) Filed: Mar. 9, 2011

(65) Prior Publication Data

US 2012/0059019 A1 Mar. 8, 2012

Related U.S. Application Data

(60) Provisional application No. 61/312,768, filed on Mar. 11, 2010.

(51) Int. Cl.
| | |
|---|---|
| *A61K 31/501* | (2006.01) |
| *A61K 31/506* | (2006.01) |
| *A61K 31/343* | (2006.01) |
| *A61K 31/422* | (2006.01) |
| *A61K 31/443* | (2006.01) |
| *C07D 405/02* | (2006.01) |
| *C07D 405/14* | (2006.01) |
| *C07D 307/84* | (2006.01) |
| *C07D 413/02* | (2006.01) |

(52) U.S. Cl. ............ 514/252.01; 514/256; 514/337; 514/374; 514/469; 544/238; 544/333; 546/282.1; 548/235; 549/467

(58) Field of Classification Search ............ 514/252.01, 514/256, 337, 374, 469; 544/238, 333; 546/282.1; 548/235; 549/467
See application file for complete search history.

(56) References Cited

U.S. PATENT DOCUMENTS

| | | | |
|---|---|---|---|
| 7,265,152 B2 | 9/2007 | Saha et al. | |
| 7,868,037 B2 | 1/2011 | Karp et al. | |
| 7,994,171 B2 * | 8/2011 | Yeung et al. ............ 514/252.01 |
| 2009/0281336 A1 | 11/2009 | Saha et al. | |
| 2010/0063068 A1 | 3/2010 | Pracitto et al. | |
| 2010/0093694 A1 | 4/2010 | Yeung et al. | |

FOREIGN PATENT DOCUMENTS

| | | |
|---|---|---|
| JP | 57-123181 | 7/1982 |
| WO | WO 02/16359 | 2/2002 |
| WO | WO 02/078701 | 10/2002 |
| WO | WO 2004/041201 | 5/2004 |
| WO | WO 2008/125874 | 10/2008 |
| WO | WO 2009/101022 | 8/2009 |
| WO | WO 2009/137493 | 11/2009 |
| WO | WO 2009/137500 | 11/2009 |
| WO | WO 2011/103063 | 8/2011 |
| WO | WO 2011/106896 | 9/2011 |
| WO | WO 2011/106929 | 9/2011 |
| WO | WO 2011/106992 | 9/2011 |

OTHER PUBLICATIONS

U.S. Appl. No. 13/031,777, filed Feb. 22, 2011, Kadow et al.
U.S. Appl. No. 13/167,356, filed Jun. 23, 2011, Yeung et al.
Database Caplus [Online], Chemical Abstracts Service, Columbus, OH, US, Grinev, A.N. et al., "Aminomethyl and aminomethyl derivatives of 5-methoxybenzofuran", Zhurnal Obshchei Khimii, 33(5):1436-1442, Coden: ZOKHA4; ISSN: 0044-460X (1963), retrieved from STN Database, Accession No. 1963:469003, RN 94004-97-4, 94623-08-2, 95220-34-1, Abstract.
Cheung, M., "The identification of pyrazolo[1,5-a]pyridines as potent p38 kinase inhibitors", Bioorganic & Medicinal Chemistry Letters, vol. 18, pp. 5428-5430 (2008).
Elsner, J. et al., "Bicyclic melatonin receptor agonists containing a ring-junction nitrogen: Synthesis, biological evaluation, and molecular modeling of the putative bioactive conformation", Bioorganic & Medicinal Chemistry, vol. 14, pp. 1949-1958 (2006).
Flint, M. et al., "Selection and Characterization of Hepatitis C Virus Replicons Dually Resistant to the Polymerase and Protease Inhibitors HCV-796 and Boceprevir (SCH 503034)", Antimicrobial Agents and Chemotherapy, vol. 53, No. 2, pp. 401-411 (2009).
Hang, J.Q. et al., "Slow Binding Inhibition and Mechanism of Resistance of Non-nucleoside Polymerase Inhibitors of Hepatitis C Virus", The Journal of Biological Chemistry, vol. 284, No. 23, pp. 15517-15529 (2009).
Kakehi, A. et al., "Preparation of New Nitrogen-Bridged Heterocycles. XIV. Further Investigation of the Desulfurization and the Rearrangement of Pyrido[1,2-d]-1,3,4-thiadiazine Intermediates", Chem. Pharm. Bull., vol. 35, No. 1, pp. 156-169 (1987).
Miki, Y. et al., "Acid-Catalyzed Reactions of 3-(Hydroxymethyl)- and 3-(1-Hydroxyethyl)pyrazolo[1,5-a]pyridines", J. Heterocyclic Chem., vol. 26, pp. 1739-1745 (1989).

* cited by examiner

*Primary Examiner* — Susannah Chung
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

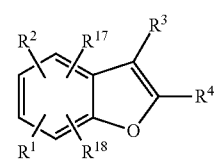

I

14 Claims, No Drawings

COMPOUNDS FOR THE TREATMENT OF HEPATITIS C

CROSS REFERENCE TO RELATED APPLICATIONS

This patent application claims the benefit of U.S. provisional patent application No. 61/312,768 filed Mar. 11, 2010.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. *N. Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N Engl.* 1 *Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201A2 describe compounds of the HCV-796 class.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I,

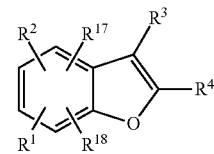

I $R^1$ is phenyl substituted with 1 $CON(R^5)(R^6)$; and where said phenyl is also substituted with 0-2 substituents selected from the group consisting of halo, cyano, alkyl, haloalkyl, hydroxyalkyl, alkoxyalkyl, (carboxy)alkyl, alkoxy, hydroxyalkyloxy, alkoxyalkyloxy, benzyloxy, $(CON(R^7)(R^8))$alkyloxy, tetrahydropyranyloxy, carboxy, alkoxycarbonyl, alkylsulfonyl, (carboxy)alkenyl, (alkoxycarbonyl)alkenyl, alkylcarboxamido, alkoxycarboxamido, alkylsulfamido, (alkylsulfamido)alkyl, $Ar^2$, and $SO_2N(R^7)(R^8)$; and where said phenyl is also substituted with 0-2 substituents selected from the group consisting of halo; nitro; alkyl; cycloalkyl; haloalkyl; aminoalkyl; hydroxyalkyl; alkoxyalkyl; hydroxy; alkoxy; $O(R^9)$; cycloalkoxy; amino; alkylamino; dialkylamino; alkylcarboxamido; alkoxycarboxamido; alkoxyalkylcarboxamido; furanyl, thienyl, pyrazolyl substituted with 0-2 alkyl substituents; pyridinyl substituted with 0-2 halo, cyano, alkyl, hydroxy, alkoxy, amino, or alkylaminocarbonyl substituents; pyrimidinyl; pyrimidinedionyl; aminopyrimidinyl; indolyl; isoquinolinyl; and phenyl substituted with 0-2 substituents selected from the group consisting of halo, alkyl, cyanoalkyl, hydroxyalkyl, alkoxyalkyl, hydroxy, alkoxy, amino, carboxy, alkoxycarbonyl, aminocarbonyl, alkylaminocarbonyl, dialkylaminocarbonyl, alkylcarboxamido, carboxyalkenyl, and phenyl;

$R^2$ is hydrogen, halo, nitro, amino, phenyl, or $(R^{10})(R^{11})N$;

$R^3$ is cyano, alkoxycarbonyl, (cycloalkyl)oxycarbonyl, (alkylsulfonyl)aminocarbonyl, $CON(R^{12})(R^{13})$, $(R^{12})(R^{13})NCONH$, triazolyl, thiazolyl, or tetrazolyl;

$R^4$ is phenyl substituted with 0-2 halo, alkoxy, phenoxy, or halophenoxy substituents;

$R^5$ is

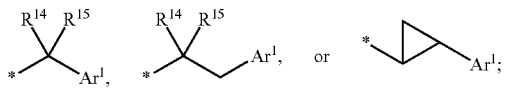

$R^6$ is hydrogen, alkyl, hydroxyalkyl, or alkoxyalkyl;
$R^7$ is hydrogen, alkyl, hydroxyalkyl, cycloalkyl, or benzyl;
$R^8$ is hydrogen or alkyl;
or $R^7$ and $R^8$ taken together with the nitrogen to which they are attached is azetidinyl, pyrrolidinyl, piperidinyl, piperazinyl, or morpholinyl;
$R^9$ is haloalkyl, cyanoalkyl, (cycloalkyl)alkyl, hydroxyalkyl, alkoxyalkyl, aminoalkyl, $(R^{16})$alkyl, $(Ar^3)$alkyl, alkynyl, or aminocycloalkyl;
$R^{10}$ is hydrogen, alkyl, or alkylsulfonyl;
$R^{11}$ is hydrogen, alkyl, hydroxyalkyl, alkoxyalkyl, or alkylsulfonyl;
$R^{12}$ is hydrogen, alkyl, or cycloalkyl;
$R^{13}$ is hydrogen, alkyl, or cycloalkyl;
or $R^{12}$ and $R^{13}$ taken together with the nitrogen to which they are attached is azetidinyl, pyrrolidinyl, piperidinyl, piperazinyl, or morpholinyl;
$R^{14}$ is hydrogen, alkyl, hydroxyalkyl, or alkoxyalkyl;
$R^{15}$ is hydrogen, alkyl, hydroxyalkyl, or alkoxyalkyl;
or $R^{14}$ and $R^{15}$ taken together is ethylene, propylene, butylene, pentylene, or hexylene;
$R^{16}$ is $CONH_2$, $H_2NCONH$, dibenzylamino, phthalimido, amino, alkylamino, dialkylamino, azetidinyl, pyrrolidinyl, piperidinyl, piperazinyl, morpholinyl where azetidinyl, pyrrolidinyl, piperidinyl, piperazinyl, or morpholinyl is substituted with 0-3 alkyl or alkoxycarbonyl substituents;
$R^{17}$ is hydrogen, halo, alkyl, or alkoxy;
$R^{18}$ is hydrogen, halo, alkyl, or alkoxy;
$Ar^1$ is azaindolyl, benzimidazolyl, azabenzimidazolyl, benzoxazolyl, oxazolopyridinyl, imidazopyridinyl, quinazolinyl, pyridopyrimidinyl or naphthyridinyl, and is substituted with 0-2 substituents selected from halo, alkyl, cycloalkyl, haloalkyl, alkoxyalkyl, hydroxy, alkoxy, amino, alkylamino, dialkylamino, aminocarbonyl, pyridinyl, phenyl, halophenyl, alkylphenyl, and alkoxyphenyl;
$Ar^2$ is phenyl, biphenyl, or pyridinyl and is substituted with 0-2 substituents selected from halo, alkyl, cyano, hydroxy, alkoxy, and carboxy; and
$Ar^3$ is furanyl, thienyl, pyrrolyl, pyrazolyl, isoxazolyl, isothiazolyl, imidazolyl, oxadiazolyl, thiadiazolyl, triazolyl, pyridinyl, indolyl, or phenyl and is substituted with 0-2 substituents selected from halo, alkyl, haloalkyl, hydroxyl, and alkoxy;
or a pharmaceutically acceptable salt thereof.

Another aspect of the invention is a compound of formula I where
$R^1$ is phenyl substituted with 1 $CON(R^5)(R^6)$ and 1 alkyl substituent;
$R^2$ is hydrogen or halo;
$R^3$ is $CON(R^{12})(R^{13})$;
$R^4$ is phenyl substituted with 0-2 halo substituents;
$R^5$ is

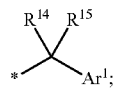

$R^6$ is hydrogen;
$R^{12}$ is alkyl;
$R^{13}$ is hydrogen;
$R^{14}$ and $R^{15}$ taken together is ethylene; and
$Ar^1$ is azaindolyl or naphthyridinyl;
or a pharmaceutically acceptable salt thereof.

Another aspect of the invention is a compound of formula I where $R^2$ is hydrogen or halo, $R^{17}$ is hydrogen, and $R^{18}$ is hydrogen.

Another aspect of the invention is a compound of formula I where $R^1$ is phenyl substituted with 1 $CON(R^5)(R^6)$ and 0-2 halo, alkyl, alkoxy, or $(CON(R^7)(R^8))$alkyloxy substituents;
$R^2$ is hydrogen or halo;
$R^3$ is $CON(R^{12})(R^{13})$;
$R^4$ is phenyl substituted with 0-2 halo substituents;
$R^5$ is

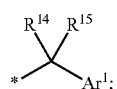

$R^6$ is hydrogen;
$R^7$ is hydrogen or alkyl;
$R^8$ is hydrogen or alkyl;
$R^{12}$ is hydrogen or alkyl;
$R^{13}$ is hydrogen or alkyl;
$R^{14}$ is hydrogen or alkyl;
$R^{15}$ is hydrogen or alkyl;
or $R^{14}$ and $R^{15}$ taken together is ethylene; and
$Ar^1$ is azaindolyl, benzimidazolyl, azabenzimidazolyl, benzoxazolyl, oxazolopyridinyl, imidazopyridinyl, quinazolinyl, pyridopyrimidinyl or naphthyridinyl;
or a pharmaceutically acceptable salt thereof.

Another aspect of the invention is a compound of formula I where $R^1$ is $R^1$ is phenyl substituted with 1 $CON(R^5)(R^6)$ and 1-2 fluoro, methyl, methoxy, or $(CONH_2)CH_2O$ substituents; $R^2$ is hydrogen or fluoro; $R^3$ is $CON(R^{12})(R^{13})$; $R^4$ is phenyl substituted with 1 fluoro substituent; $R^5$ is

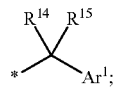

$R^6$ is hydrogen; $R^{12}$ is methyl; $R^{13}$ is hydrogen; $R^{14}$ is methyl, $R^{15}$ is hydrogen; or $R^{14}$ and $R^{15}$ taken together is ethylene; and $Ar^1$ is azaindolyl, benzimidazolyl, azabenzimidazolyl, benzoxazolyl, oxazolopyridinyl, imidazopyridinyl, quinazolinyl, pyridopyrimidinyl or naphthyridinyl; or a pharmaceutically acceptable salt thereof.

Another aspect of the invention is a compound of formula I where $R^1$ is phenyl substituted with 1 $CON(R^5)(R^6)$ and 1-2 fluoro, methyl, or methoxy substituents; $R^2$ is hydrogen or fluoro; $R^3$ is $CON(R^{12})(R^{13})$; $R^4$ is 4-fluorophenyl; $R^5$ is

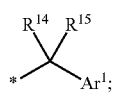

$R^6$ is hydrogen; $R^{12}$ is methyl; $R^{13}$ is hydrogen; $R^{14}$ and $R^{15}$ taken together is ethylene; and $Ar^1$ is azaindolyl, benzimidazolyl, azabenzimidazolyl, benzoxazolyl, oxazolopyridinyl, imidazopyridinyl, quinazolinyl, pyridopyrimidinyl or naphthyridinyl; or a pharmaceutically acceptable salt thereof.

Another aspect of the invention is a compound of formula I where $R^1$ is phenyl substituted with 1 $CON(R^5)(R^6)$; and where said phenyl is also substituted with 0-2 substituents selected from the group consisting of halo, cyano, alkyl, haloalkyl, hydroxyalkyl, alkoxyalkyl, (carboxy)alkyl, alkoxy, hydroxyalkyloxy, alkoxyalkyloxy, benzyloxy, (CON($R^7$)($R^8$))alkyloxy, tetrahydropyranyloxy, carboxy, alkoxycarbonyl, alkylsulfonyl, (carboxy)alkenyl, (alkoxycarbonyl)alkenyl, alkylcarboxamido, alkoxycarboxamido, alkylsulfamido, (alkylsulfamido)alkyl, $Ar^2$, and $SO_2N(R^7)(R^8)$; and where said phenyl is also substituted with 0-2 substituents selected from the group consisting of halo; nitro; alkyl; cycloalkyl; haloalkyl; aminoalkyl; hydroxyalkyl; alkoxyalkyl; hydroxy; alkoxy; O($R^9$); cycloalkoxy; amino; alkylamino; dialkylamino; alkylcarboxamido; alkoxycarboxamido; alkoxyalkylcarboxamido; furanyl, thienyl, pyrazolyl substituted with 0-2 alkyl substituents; pyridinyl substituted with 0-2 halo, cyano, alkyl, hydroxy, alkoxy, amino, or alkylaminocarbonyl substituents; pyrimidinyl; pyrimidinedionyl; aminopyrimidinyl; indolyl; isoquinolinyl; and phenyl substituted with 0-2 substituents selected from the group consisting of halo, alkyl, cyanoalkyl, hydroxyalkyl, alkoxyalkyl, hydroxy, alkoxy, amino, carboxy, alkoxycarbonyl, aminocarbonyl, alkylaminocarbonyl, dialkylaminocarbonyl, alkylcarboxamido, carboxyalkenyl, and phenyl; $R^2$ is hydrogen, halo, or $(R^{10})(R^{11})N$; $R^3$ is cyano, alkoxycarbonyl, (cycloalkyl)oxycarbonyl, (alkylsulfonyl)aminocarbonyl, $CON(R^{12})(R^{13})$, $(R^{12})(R^{13})NCONH$, triazolyl, thiazolyl, or tetrazolyl; $R^4$ is phenyl substituted with 0-2 halo, alkoxy, phenoxy, or halophenoxy substituents; $R^5$ is

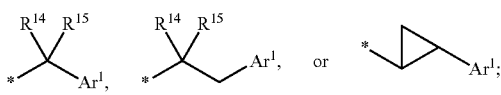

$R^6$ is hydrogen, alkyl, hydroxyalkyl, or alkoxyalkyl; $R^7$ is hydrogen, alkyl, hydroxyalkyl, cycloalkyl, or benzyl; $R^8$ is hydrogen or alkyl; or $R^7$ and $R^8$ taken together with the nitrogen to which they are attached is azetidinyl, pyrrolidinyl, piperidinyl, piperazinyl, or morpholinyl; $R^9$ is haloalkyl, cyanoalkyl, (cycloalkyl)alkyl, hydroxyalkyl, alkoxyalkyl, aminoalkyl, $(R^{16})$alkyl, $(Ar^3)$alkyl, alkynyl, or aminocycloalkyl; $R^{10}$ is alkylsulfonyl; $R^{11}$ is hydrogen, alkyl, hydroxyalkyl, or alkoxyalkyl; $R^{12}$ is hydrogen, alkyl, or cycloalkyl; $R^{13}$ is hydrogen, alkyl, or cycloalkyl; or $R^{12}$ and $R^{13}$ taken together with the nitrogen to which they are attached is azetidinyl, pyrrolidinyl, piperidinyl, piperazinyl, or morpholinyl; $R^{14}$ is hydrogen, alkyl, hydroxyalkyl, or alkoxyalkyl; $R^{15}$ is hydrogen, alkyl, hydroxyalkyl, or alkoxyalkyl; or $R^{14}$ and $R^{15}$ taken together is ethylene, propylene, butylene, pentylene, or hexylene; $R^{16}$ is $CONH_2$, $H_2NCONH$, dibenzylamino, phthalimido, amino, alkylamino, dialkylamino, azetidinyl, pyrrolidinyl, piperidinyl, piperazinyl, morpholinyl where azetidinyl, pyrrolidinyl, piperidinyl, piperazinyl, or morpholinyl is substituted with 0-3 alkyl or alkoxycarbonyl substituents; $R^{17}$ is hydrogen, fluoro, or chloro; $R^{18}$ is hydrogen, fluoro, or chloro; $Ar^1$ is azaindolyl, benzimidazolyl, azabenzimidazolyl, benzoxazolyl, oxazolopyridinyl, imidazopyridinyl, quinazolinyl, pyridopyrimidinyl or naphthyridinyl, and is substituted with 0-2 substituents selected from halo, alkyl, cycloalkyl, haloalkyl, alkoxyalkyl, hydroxy, alkoxy, amino, alkylamino, dialkylamino, aminocarbonyl, pyridinyl, phenyl, halophenyl, alkylphenyl, and alkoxyphenyl; $Ar^2$ is phenyl, biphenyl, or pyridinyl and is substituted with 0-2 substituents selected from halo, alkyl, cyano, hydroxy, alkoxy, and carboxy; and $Ar^3$ is furanyl, thienyl, pyrrolyl, pyrazolyl, isoxazolyl, isothiazolyl, imidazolyl, oxadiazolyl, thiadiazolyl, triazolyl, pyridinyl, indolyl, or phenyl and is substituted with 0-2 substituents selected from halo, alkyl, haloalkyl, hydroxyl, and alkoxy; or a pharmaceutically acceptable salt thereof. Another aspect of the invention is a compound of this formula where $R^{17}$ and $R^{18}$ are hydrogen.

Another aspect of the invention is a compound of formula I where $R^1$ is phenyl substituted with 1 $CON(R^5)(R^6)$ substituent and also substituted with 0-2 halo, alkyl, or alkoxy substituents.

Another aspect of the invention is a compound of formula I where $R^5$ is

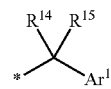

and $R^{14}$ and $R^{15}$ is ethylene or propylene.

Another aspect of the invention is a compound of formula I where $R^5$ is

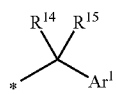

and $R^{14}$ and $R^{15}$ is ethylene.

Another aspect of the invention is a compound of formula I where $R^5$ is

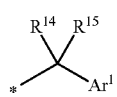

and at least one of $R^{14}$ and $R^{15}$ is not hydrogen.

Another aspect of the invention is a compound of formula I where $Ar^1$ is azaindolyl, benzimidazolyl, azabenzimidazolyl, benzoxazolyl, oxazolopyridinyl, imidazopyridinyl, quinazolinyl, pyridopyrimidinyl or naphthyridinyl, and is substituted with 0-2 substituents selected from halo, alkyl, cycloalkyl, haloalkyl, alkoxyalkyl, hydroxy, alkoxy, amino, alkylamino, dialkylamino, aminocarbonyl, pyridinyl, phenyl, halophenyl, alkylphenyl, and alkoxyphenyl.

Another aspect of the invention is a compound of formula I where $Ar^1$ is azaindolyl, benzimidazolyl, azabenzimidazolyl, benzoxazolyl, oxazolopyridinyl, imidazopyridinyl, quinazolinyl, pyridopyrimidinyl or naphthyridinyl.

Another aspect of the invention is a compound of formula I where $R^3$ is $CON(R^{11})(R^{12})$.

Another aspect of the invention is a compound of formula I where $R^3$ is CON(H)(alkyl).

Another aspect of the invention is a compound of formula I where $R^4$ is halophenyl.

Another aspect of the invention is a compound of formula I where $R^4$ is phenyl or monofluorophenyl.

Another aspect of the invention is a compound of formula I where $Ar^1$ is phenyl.

Any scope of any variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $Ar^1$, $Ar^2$, or $Ar^3$ can be used independently with the scope of any other instance of a variable.

Unless specified otherwise, these terms have the following meanings.

"Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append. For example, substituents $R^1$ and $R^2$ of formula IV are intended to bond to the benzene ring of formula IV and not to the thiophene ring.

Ethylene means ethanediyl or —CH$_2$CH$_2$—; propylene means propanediyl or —CH$_2$CH$_2$CH$_2$—; butylene means butanediyl or —CH$_2$CH$_2$CH$_2$CH$_2$—; pentylene means pentanediyl or —CH$_2$CH$_2$CH$_2$CH$_2$CH$_2$—.

Dioxothiazinyl means

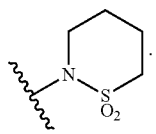

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms. The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

As shown in Scheme 1, some compounds of the invention may be prepared by coupling a benzofuran triflate or halide to a substituted phenyl boronic acid that in some examples contains a carboxylic acid or carboxylic acid ester. Other coupling techniques and conditions are also known in the art as are other carbon-carbon bond forming reactions. Acids and esters may be converted to amides by methods known in the art.

Scheme 1.

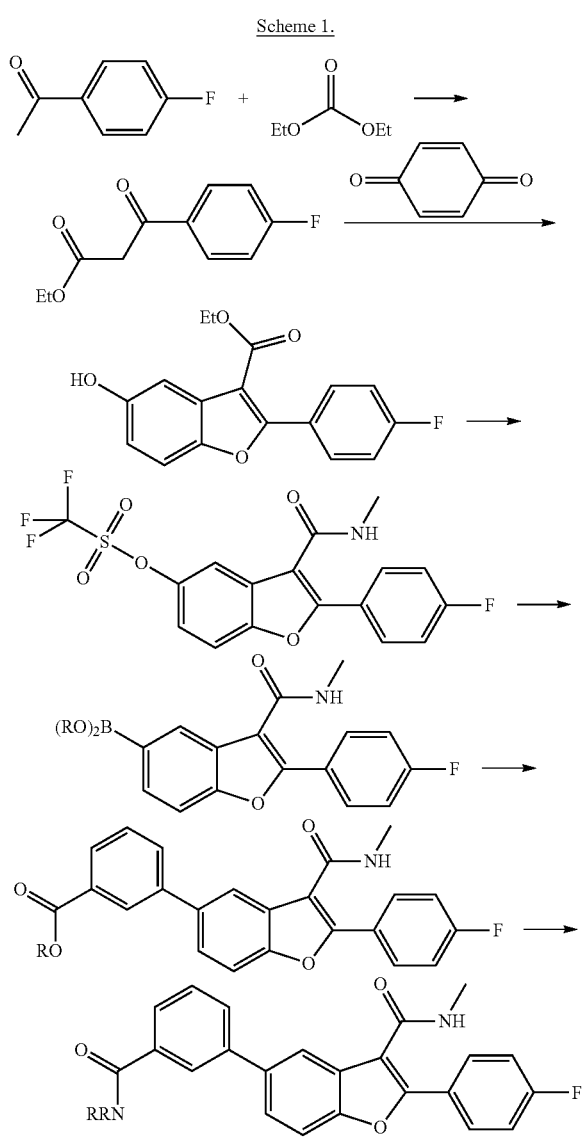

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3 L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (14 nM) was added to diluted compound followed by the addition of a mixture of template (0.2 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH₂O, NaCl added to 150 mM final, the FRET peptide diluted to 20 µM final from a 2 mM stock.

To prepare plates, HCV replicon cells, with or without a *Renilla* luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

HCV Replicon Luciferase Reporter Assay

The HCV replicon luciferase assay was developed to monitor the inhibitory effects of compounds described in the disclosure on HCV viral replication. Utilization of a replicon luciferase reporter assay was first described by Krieger et al (Krieger N, Lohmann V, and Bartenschlager R, *J. Virol.* 75(10):4614-4624 (2001)). HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 µl of cells at a density of $3.0 \times 10^3$ cells/well in DMEM containing 4% FCS (final DMSO concentration at 0.5%). After 3 days incubation at 37° C., cells were analyzed for *Renilla* Luciferase activity using the EnduRen as substrate (Promega cat #E6485). The EnduRen substrate was diluted in DMEM and then added to the plates to a final concentration of 7.5 µM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat #G8082). 3 µl of Cell-Titer Blue was added to each well and incubated for 8 hrs at 37° C. The fluorescence signal from each well was read, with an excitation wavelength at 525/10 nm and an emission wavelength of 598/10 nm, using the Viewlux Imager.

Representative data for compounds are reported in Table 1.

TABLE 1

| Structure | $IC_{50}$ (µM) | $EC_{50}$ (µM) |
|---|---|---|
| 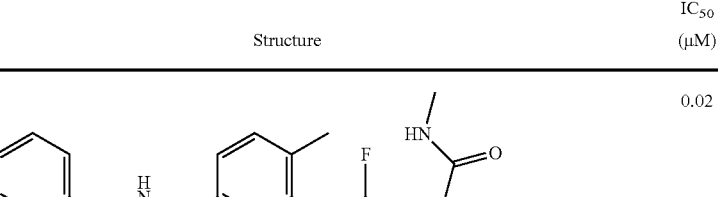 | 0.02 | 0.007 |
| 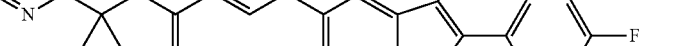 |  | 0.06 |

TABLE 1-continued
| Structure | IC$_{50}$ (μM) | EC$_{50}$ (μM) |
|---|---|---|
| 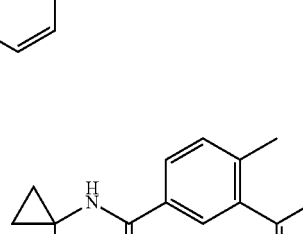 | 0.003 | 0.04 |
| 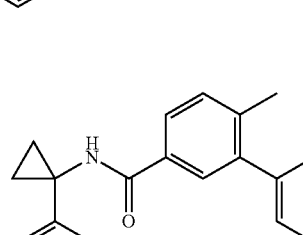 | 0.005 | 0.21 |
| 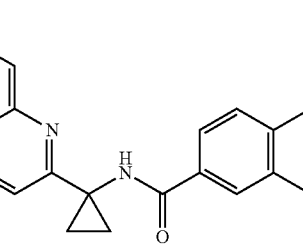 | 0.005 | 0.003 |
| 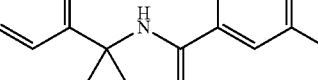 | 0.02 | 0.006 |
| 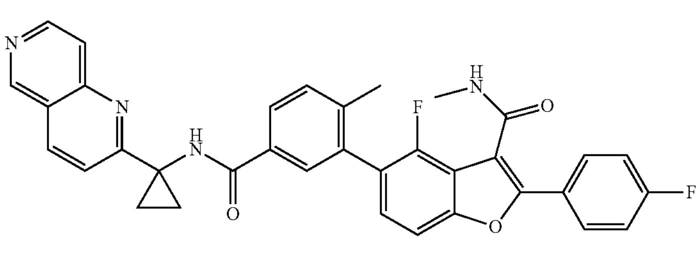 [SMILES: CNC(=O)c1c(-c2ccc(F)cc2)oc2ccc(-c3cc(C(=O)NC4(c5ccc6cnccc6n5)CC4)ccc3C)c(F)c12] | 0.01 | 0.004 |

TABLE 1-continued

| Structure | IC$_{50}$ (μM) | EC$_{50}$ (μM) |
|---|---|---|
| 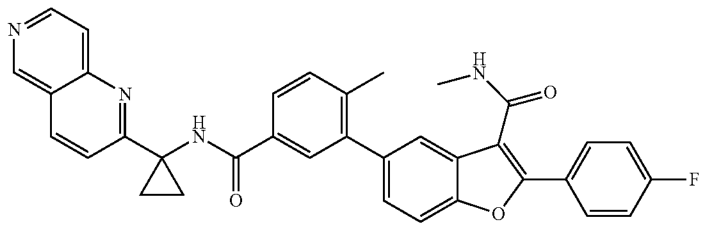 | 0.008 | 0.002 |
| | 0.01 | 0.009 |
| | 0.01 | 0.07 |
| 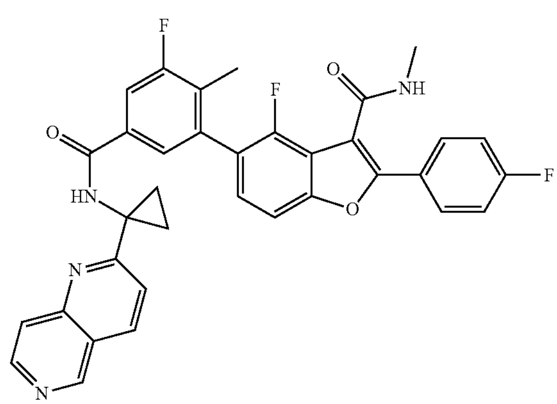 [SMILES: CNC(=O)c1c(-c2ccc(F)cc2)oc2ccc(-c3cc(C(=O)NC4(c5ccc6cnccc6n5)CC4)cc(F)c3C)c(F)c12] | 0.007 | 0.006 |

TABLE 1-continued
| Structure | IC$_{50}$ (μM) | EC$_{50}$ (μM) |
|---|---|---|
| 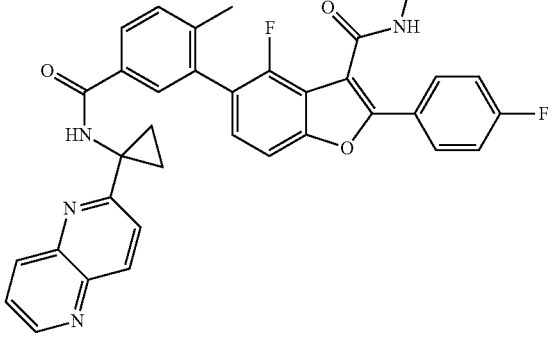 | 0.01 | 0.03 |
| 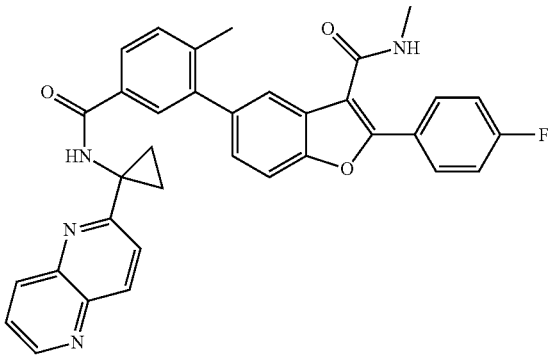 [SMILES: CNC(=O)c1c(-c2ccc(F)cc2)oc2ccc(-c3cc(C(=O)NC4(c5ccc6ncccc6n5)CC4)ccc3C)cc12] | 0.01 | 0.03 |
| 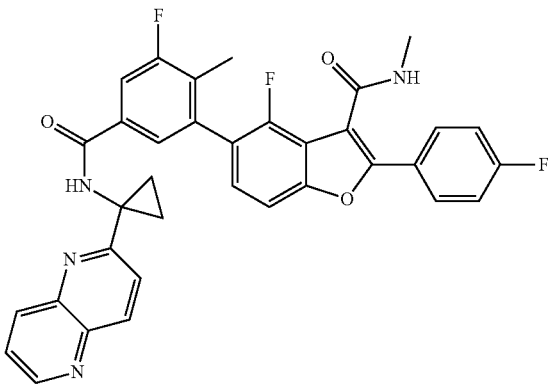 [SMILES: CNC(=O)c1c(-c2ccc(F)cc2)oc2ccc(-c3cc(C(=O)NC4(c5ccc6ncccc6n5)CC4)cc(F)c3C)c(F)c12] | 0.07 | 0.10 |
| 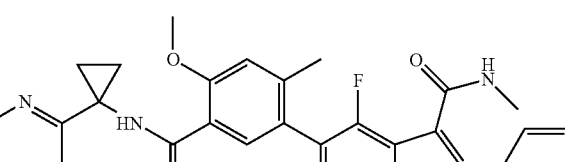 | 0.10 | 0.009 |
| 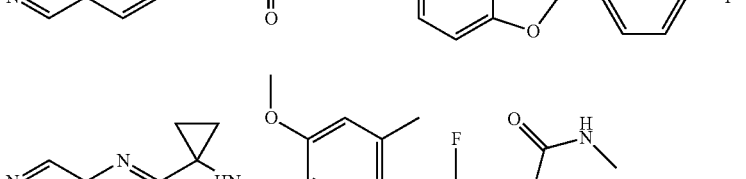 | 0.03 | 0.006 |

TABLE 1-continued
| Structure | IC$_{50}$ (μM) | EC$_{50}$ (μM) |
|---|---|---|
| 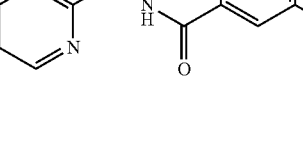 | 0.02 | 0.002 |
| 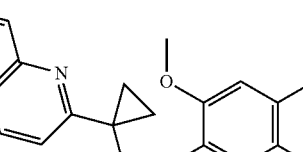 | 0.005 | 0.004 |
| 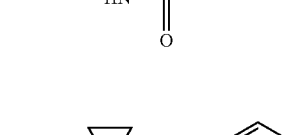 | 0.006 | 0.02 |
| 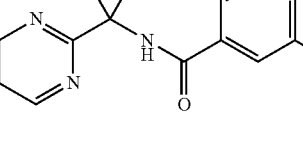 | 0.02 | 0.004 |
| 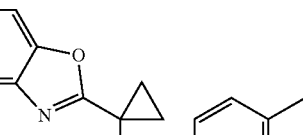 | 0.02 | 0.006 |
| 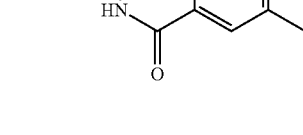 | 0.04 | 0.001 |

TABLE 1-continued
| Structure | IC$_{50}$ (μM) | EC$_{50}$ (μM) |
|---|---|---|
| 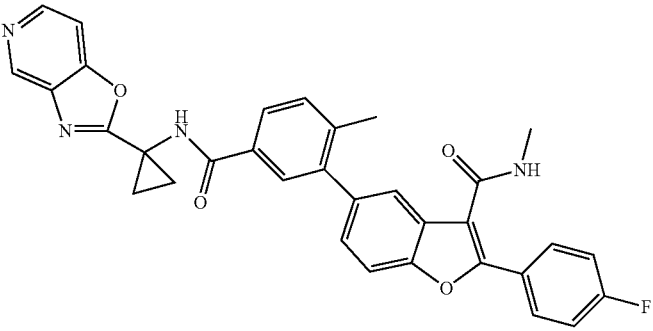 [SMILES: CNC(=O)c1c(-c2ccc(F)cc2)oc2ccc(-c3cc(C(=O)NC4(c5nc6cnccc6o5)CC4)ccc3C)cc12] | 0.02 | 0.001 |
| 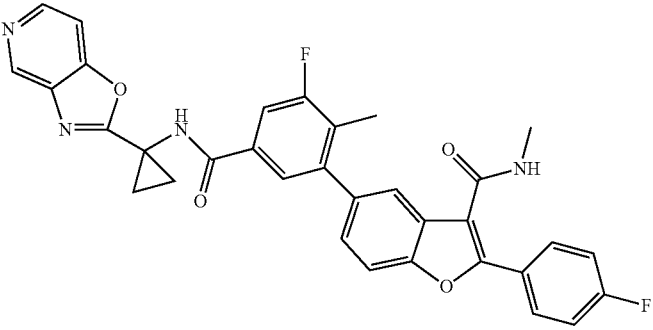 [SMILES: CNC(=O)c1c(-c2ccc(F)cc2)oc2ccc(-c3cc(C(=O)NC4(c5nc6cnccc6o5)CC4)cc(F)c3C)cc12] | 0.02 | 0.003 |
| 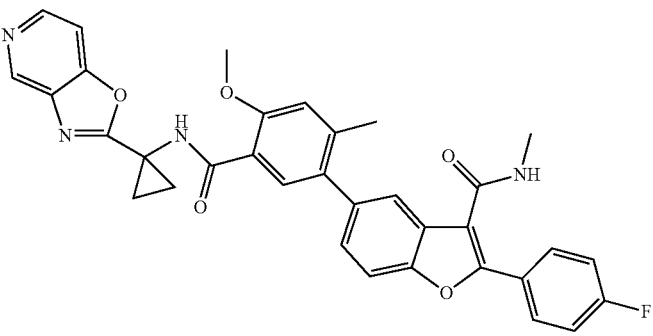 [SMILES: CNC(=O)c1c(-c2ccc(F)cc2)oc2ccc(-c3cc(C(=O)NC4(c5nc6cnccc6o5)CC4)c(OC)cc3C)cc12] | 0.01 | 0.001 |
| 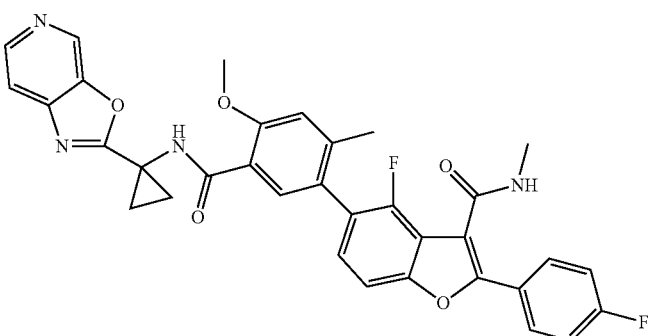 | 0.02 | 0.004 |
| Chiral 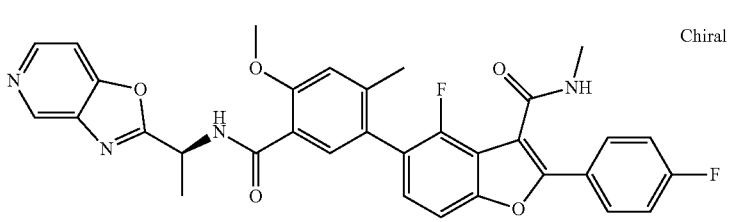 [SMILES: CNC(=O)c1c(-c2ccc(F)cc2)oc2ccc(-c3cc(C(=O)N[C@@H](C)c4nc5cnccc5o4)c(OC)cc3C)c(F)c12] | 0.06 | 0.02 |

TABLE 1-continued
| Structure | | IC$_{50}$ (μM) | EC$_{50}$ (μM) |
|---|---|---|---|
| 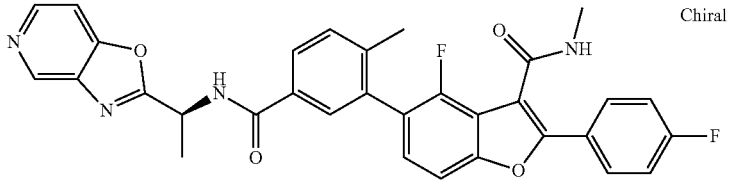 [SMILES: CNC(=O)c1c(-c2ccc(F)cc2)oc2ccc(-c3cc(C(=O)N[C@@H](C)c4nc5cnccc5o4)ccc3C)c(F)c12] | Chiral | 0.03 | 0.03 |
| 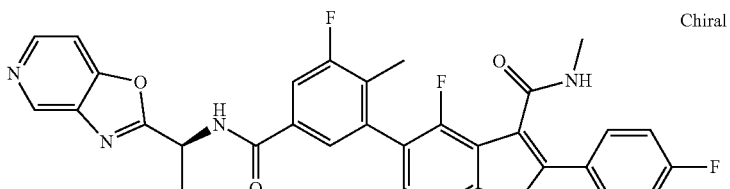 | Chiral | 0.06 | 0.02 |
| 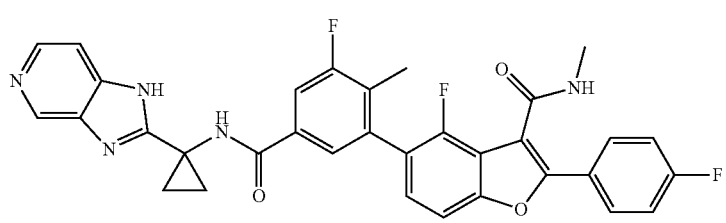 [SMILES: CNC(=O)c1c(-c2ccc(F)cc2)oc2ccc(-c3cc(C(=O)NC4(c5nc6cnccc6[nH]5)CC4)cc(F)c3C)c(F)c12] | | 0.01 | 0.007 |
| 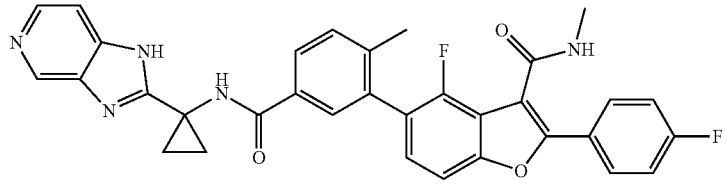 [SMILES: CNC(=O)c1c(-c2ccc(F)cc2)oc2ccc(-c3cc(C(=O)NC4(c5nc6cnccc6[nH]5)CC4)ccc3C)c(F)c12] | | 0.01 | 0.006 |
| 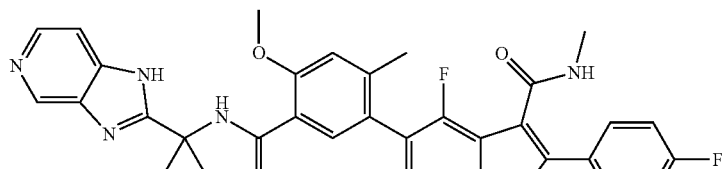 | | 0.02 | 0.005 |
| 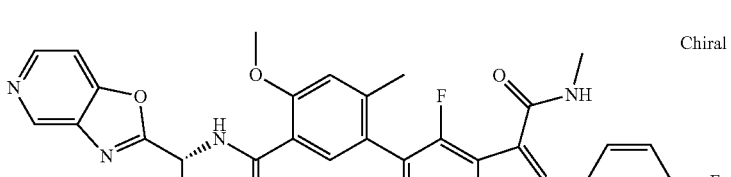 | Chiral | 0.04 | 0.01 |
| 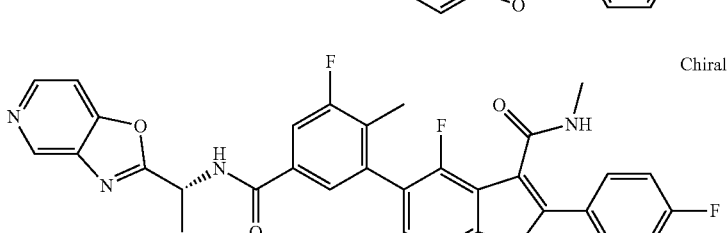 | Chiral | 0.03 | 0.04 |

TABLE 1-continued

| Structure | | IC$_{50}$ (μM) | EC$_{50}$ (μM) |
|---|---|---|---|
| 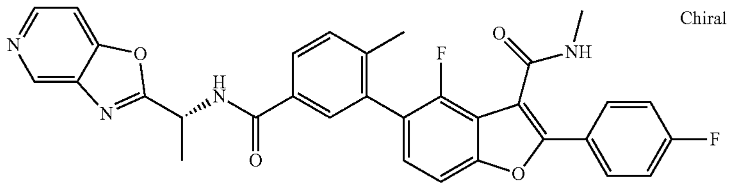 [SMILES: CNC(=O)c1c(-c2ccc(F)cc2)oc2ccc(-c3cc(C(=O)N[C@H](C)c4nc5cnccc5o4)ccc3C)c(F)c12] | Chiral | 0.02 | 0.02 |

If no data is entered use the following key: A 0.002 or less to 0.25 μM; B>0.25 μM-<1.0 μM; C 1.0 μM-10.0 μM; D>0.67 μM but an exact value was not determined; E>10.0 μM; F>0.4 μM; but an exact value was not determined; G>1.39 μM but an exact value was not determined; H>0.62 μM but an exact value was not determined; I>4 μM but an exact value was not determined; J>3.7 μM but an exact value was not determined; K>1.23 μM but an exact value was not determined; L>4.17 μM but an exact value was not determined; M>0.5 μM but an exact value was not determined.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
| --- | --- | --- |
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/Eli Lilly and Co. Inc., Indianapolis, IN |

TABLE 2-continued

| Brand Name | Type of Inhibitor or Target | Source Company |
|---|---|---|
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 May 26, 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS 1-(1,8-naphthyridin-2-yl)cyclopropanamine was prepared according to the four step synthesis as briefly depicted below.

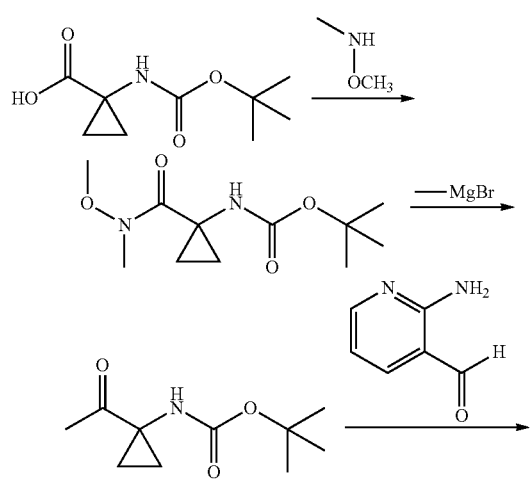

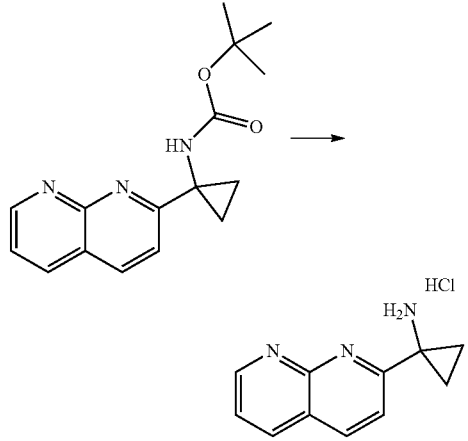

tert-butyl 1-(methoxy(methyl)carbamoyl)cyclopropylcarbamate. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. White solid, 58.7% yield. LCMS m/z 245.2 (M+H), rt=1.768 min., 100% purity. $^1$H NMR (400 MHz, DMSO-d6) δ ppm 0.70-0.94 (m, 2H), 1.09-1.24 (m, 2 H), 1.38 (s, 9H), 3.06 (s, 3 H), 3.64 (s, 3 H), 7.55 (br. s., 1 H).

tert-butyl 1-acetylcyclopropylcarbamate. White solid, 91% yield, 90% purity. $^1$H NMR (400 MHz, DMSO-d$_6$) δ ppm 0.99 (q, J=4.10 Hz, 2H), 1.29 (q, J=4.10 Hz, 2 H), 1.39 (s, 9 H), 2.13 (s, 3 H), 7.73 (br. s., 1 H).

tert-butyl 1-(1,8-naphthyridin-2-yl)cyclopropylcarbamate. The LC/MS data was obtained on a Shimadzu analytical LC/Micromass Platform LC (ESI+) at 220 nm using the following set of conditions: Phenomenex Luna 3 nm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. White solid, 47.2% yield. LCMS rt=1.573 min, m/z 286.2 (M+H), 100% purity. $^1$H NMR (400 MHz, CD$_3$OD) δ ppm 1.40-1.47 (m, 2H), 1.56 (s, 9 H), 1.88-1.98 (m, 2 H), 7.60 (dd, J=8.03, 4.52 Hz, 1 H), 7.82 (d, J=8.53 Hz, 1 H), 8.38 (d, J=8.53 Hz, 1 H), 8.44 (d, J=8.03 Hz, 1 H), 9.01 (dd, J=4.27, 1.76 Hz, 1 H).

1-(1,8-naphthyridin-2-yl)cyclopropanamine, HCl. The LC/MS data was obtained on a Shimadzu analytical LC/Micromass Platform LC (ESI+) at 220 nm using the following set of conditions: Phenomenex Luna 3 nm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. White solid, 97% yield. LCMS rt=0.435 min, m/z 186.1 (M+H), 99.4% purity. $^1$H NMR (400 MHz, DMSO-d$_6$) δ ppm 1.95 (d, J=2.51 Hz, 4H), 7.76 (d, J=9.03 Hz, 1 H), 8.25 (dd, J=8.28, 5.52 Hz, 1 H), 8.89 (d, J=8.78 Hz, 1H), 9.35 (dd, J=8.28, 1.51 Hz, 1 H), 9.41 (dd, 1 H).

1-(1,7-naphthyridin-2-yl)cyclopropanamine, HCl. 1-(1,7-naphthyridin-2-yl)cyclopropanamine, HCl was synthesized in a similar fashion.

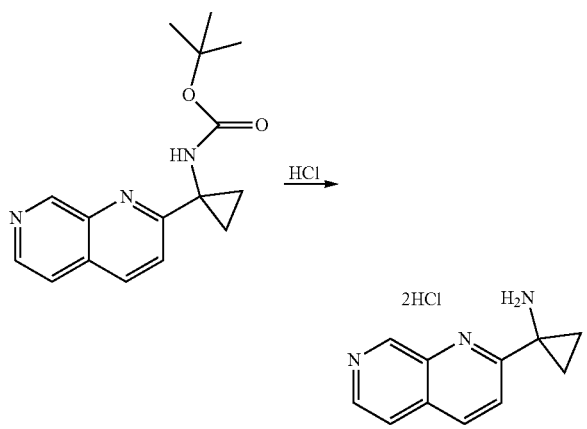

The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. Tan solid, 52.6% yield. LCMS rt=0.460 min., m/z 186.1 (M+H), 98.3% purity. $^1$H NMR (400 MHz, CD$_3$OD) δ ppm 1.91 (s, 4 H), 7.86 (d, J=9.03 Hz, 1 H), 8.65 (d, J=6.27 Hz, 1 H), 8.75-8.90 (m, 2 H), 9.91 (s, 1 H).

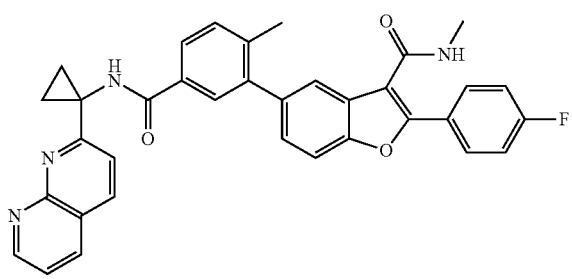 [SMILES: CNC(=O)c1c(-c2ccc(F)cc2)oc2ccc(-c3cc(C(=O)NC4(c5ccc6cccnc6n5)CC4)ccc3C)cc12]

5-(5-(1-(1,8-naphthyridin-2-yl)cyclopropylcarbamoyl)-2-methylphenyl)-2-(4-fluorophenyl)-N-methylbenzofuran-3-carboxamide. To a 1 dram vial was added 3-(2-(4-fluorophenyl)-3-(methylcarbamoyl)benzofuran-5-yl)-4-methylbenzoic acid (30.3 mg, 0.075 mmol) in DMF (1 mL) along with N-ethyl-N-isopropylpropan-2-amine (0.065 mL, 0.375 mmol), 1-(1,8-naphthyridin-2-yl)cyclopropanamine, HCl (31.1 mg, 0.113 mmol) and finally HATU (2-(3H-[1,2,3]triazolo[4,5-b]pyridin-3-yl)-1,1,3,3-tetramethyl isouronium hexafluorophosphate(V), (114 mg, 0.300 mmol). The vial was sealed and the tan mixture shaken overnight at room temperature. The crude product was purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Waters Sunfire 5 μm C18 19×150 mm column at a gradient of 20-100% B and a flow rate of 25 mL/min. over 22 minutes with a 8 minute hold. The solvent was removed giving 45.0 mgs (87% yield) of 5-(5-(1-(1,8-naphthyridin-2-yl)cyclopropylcarbamoyl)-2-methylphenyl)-2-(4-fluorophenyl)-N-methylbenzofuran-3-carboxamide, TFA as a tan solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Xbridge Phenyl C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.44 (q, J=4.18 Hz, 2 H), 1.90-1.98 (m, 2 H), 2.30 (s, 3 H), 2.89 (d, J=4.77 Hz, 3 H), 7.18-7.26 (m, 2 H), 7.29 (dd, J=8.28, 1.76 Hz, 1 H), 7.34-7.39 (m, 1 H), 7.50 (dd, J=8.03, 4.52 Hz, 2 H), 7.57 (d, J=8.53 Hz, 1H), 7.69 (d, J=1.25 Hz, 1H), 7.74 (d, J=8.53 Hz, 1 H), 7.85-7.91 (m, 2H), 8.07-8.14 (m, 2 H), 8.18 (d, J=8.53 Hz, 1 H), 8.34 (dd, J=8.03, 1.76 Hz, 1 H), 8.73 (s, 1 H), 9.04 (dd, 1 H). LCMS rt=1.430 min., m/z 571.3 (M+H), 98.3% purity. HPLC (Sunfire C18) rt=6.931 min, 99.4% purity and (XBridge Phenyl C18) rt=11.521 min., 100% purity.

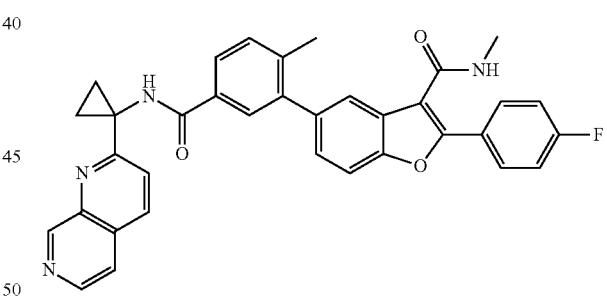

5-(5-(1-(1,7-naphthyridin-2-yl)cyclopropylcarbamoyl)-2-methylphenyl)-2-(4-fluorophenyl)-N-methylbenzofuran-3-carboxamide. 5-(5-(1-(1,7-naphthyridin-2-yl)cyclopropylcarbamoyl)-2-methylphenyl)-2-(4-fluorophenyl)-N-methylbenzofuran-3-carboxamide was synthesized in a similar fashion. $^1$H NMR (400 MHz, THF-d8) δ ppm 1.51-1.59 (m, 2 H), 1.90-1.95 (m, 2 H), 2.32 (s, 3 H), 2.89 (d, J=4.77 Hz, 3H), 7.18-7.27 (m, 2 H), 7.32 (dd, J=8.41, 1.63 Hz, 1 H), 7.36-7.42 (m, 1 H), 7.46 (d, J=4.27 Hz, 1 H), 7.59 (d, J=8.28 Hz, 1 H), 7.70 (d, J=1.25 Hz, 1H), 7.86-7.93 (m, 2 H), 8.03-8.17 (m, 3 H), 8.28 (br. s., 1 H), 8.40 (d, J=9.04 Hz, 1H), 8.63 (br. s., 1 H), 8.79 (s, 1 H), 9.51 (s, 1 H). LCMS rt=2.603 min., m/z 571.3 (M+H), 98.4% purity. HPLC rt=7.121 min. (Sunfire C18), 99.3% purity and 11.708 min. (XBridge Phenyl C18), 95.9% purity.

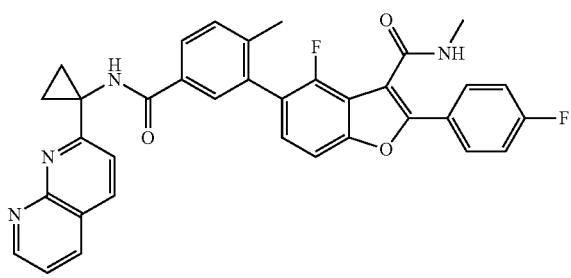 [SMILES: CNC(=O)c1c(-c2ccc(F)cc2)oc2ccc(-c3cc(C(=O)NC4(c5ccc6cccnc6n5)CC4)ccc3C)c(F)c12]

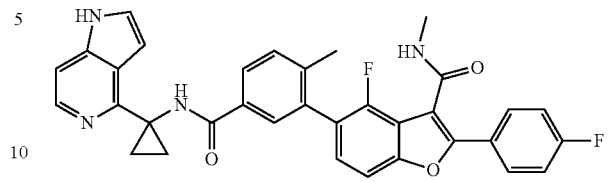

5-(5-(1-(1,8-naphthyridin-2-yl)cyclopropylcarbamoyl)-2-methylphenyl)-4-fluoro-2-(4-fluoro phenyl)-N-methylbenzofuran-3-carboxamide. To a 25 mL RBF was added 3-(4-fluoro-2-(4-fluorophenyl)-3-(methylcarbamoyl)benzofuran-5-yl)-4-methylbenzoic acid (20.5 mg, 0.049 mmol) in DMF (1 mL) along with N-ethyl-N-isopropylpropan-2-amine (0.042 mL, 0.243 mmol), 1-(1,8-naphthyridin-2-yl)cyclopropanamine, HCl (20.17 mg, 0.073 mmol) and finally 5 eq. of HATU, 2-(3H-[1,2,3]triazolo[4,5-b]pyridin-3-yl)-1,1,3,3-tetramethylisouronium hexafluorophosphate(V) (74.0 mg, 0.195 mmol). The flask was sealed with a septa, placed under nitrogen and the mixture stirred overnight at room temperature. The crude product was purified using a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Phenomenex Luna 10 μm C18 30×100 mm column at a gradient of 40-100% B and a flow rate of 40 mL/min. over 12 minutes with a 13 minute hold. The solvent was removed giving 33.3 mgs (96% yield) of 5-(5-(1-(1,8-naphthyridin-2-yl)cyclopropylcarbamoyl)-2-methylphenyl)-4-fluoro-2-(4-fluorophenyl)-N-methylbenzofuran-3-carboxamide, TFA as a yellow powder. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Xbridge Phenyl C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.40-1.49 (m, 2H), 1.95 (m, 2 H), 2.25 (s, 3 H), 2.88 (m, 3 H), 7.17-7.29 (m, 3 H), 7.37-7.47 (m, 2 H), 7.50 (dd, J=8.03, 4.52 Hz, 1 H), 7.74 (m, 2 H), 7.85-7.97 (m, 2 H), 8.03-8.09 (m, 2 H), 8.18 (d, J=8.53 Hz, 1 H), 8.33-8.39 (m, 1 H), 8.74 (s, 1 H), 9.05 (dd, J=4.27, 1.76 Hz, 1 H). LCMS rt=2.475 min, m/z 589.3 (M+H), 95.7% purity. HPLC rt=6.728 min. (Sunfire C18), 100% purity and 11.261 min. (XBridge C18), 99.0% purity.

5-(5-(1-(1H-pyrrolo[3,2-d]pyridin-4-yl)cyclopropylcarbamoyl)-2-methylphenyl)-4-fluoro-2-(4-fluorophenyl)-N-methylbenzofuran-3-carboxamide. This example was prepared from the coupling of 3-(4-fluoro-2-(4-fluorophenyl)-3-(methylcarbamoyl)benzofuran-5-yl)-4-methylbenzoic acid with 1-(1H-pyrrolo[3,2-c]pyridin-4-yl)cyclopropanamine (obtained from 1H-pyrrolo[3,2-c]pyridine-4-carbonitrile by the reaction using Ti(OiPr)$_4$/EtMgBr/BF$_3$OEt$_2$). Purification was performed by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=10, Final % B=100, Gradient time=10 min, Stop time=12 min, Flow Rate=25 mL/min, Column: Sunfire Prep C18 19×100 5 um, Fraction Collection: 7.86-8.40 min. (UV detection at 220 nm). The material obtained was further purified by preparative TLC (500 um×20×20 cm plate, 10% MeOH/CH$_2$Cl$_2$). Analytical TLC Rf=0.30 (10% MeOH/CH$_2$Cl$_2$). $^1$H NMR (500 MHz, CD$_3$OD) δ 8.05 (d, J=5.80, 1H), 7.94 (m, 2H), 7.86 (d, J=7.93, 1H), 7.80 (s, 1H), 7.53 (d, J=8.55, 1H), 7.46 (d, J=8.24, 1H), 7.37 (d, J=3.36, 2H), 7.31-7.27 (overlapping m, 3H), 6.93 (d, J=3.05, 1H), 2.95 (s, 3H), 2.28 (s, 3H), 1.77 (m, 2H), 1.47 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=577.25, HPLC R$_t$=1.427 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=20, Final % B=100, Gradient time=15 min, Stop time=18 min, Flow Rate=1 ml/min, Column: Sunfire C18, 3.5 um, 4.6×150 mm, R$_t$=8.06 min; Column: Xbridge Phenyl 3.5 um, 4.6×150 mm, R$_t$=8.78 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=10.20 min.

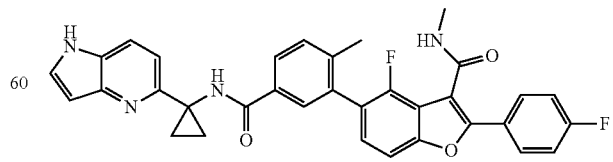

5-(5-(1-(1H-pyrrolo[3,2-b]pyridin-5-yl)cyclopropylcarbamoyl)-2-methylphenyl)-4-fluoro-2-(4-fluorophenyl)-N-methylbenzofuran-3-carboxamide. This example was prepared from the coupling of 3-(4-fluoro-2-(4-fluorophenyl)-3-(methylcarbamoyl)benzofuran-5-yl)-4-methylbenzoic acid with 1-(1H-pyrrolo[3,2-b]pyridin-5-yl)cyclopropanamine (obtained from 1H-pyrrolo[3,2-b]pyridine-5-carbonitrile by the reaction using Ti(OiPr)$_4$/EtMgBr/BF$_3$OEt$_2$). Purification was performed by Shimadzu-VP preparative reverse phase HPLC using the separation method: Solvent A=10% MeOH-90% H$_2$O-0.1% TFA, Solvent B=90% MeOH-10% H$_2$O-0.1% TFA, Start % B=10, Final % B=100, Gradient time=10 min, Stop time=12 min, Flow Rate=25 mL/min, Column: Sunfire Prep C18 19×100 5 um, Fraction Collection: 7.86-8.38 min. (UV detection at 220 nm). The material obtained was further purified by preparative TLC (500 um×20×20 cm plate, 5% MeOH/CH$_2$Cl$_2$). Analytical TLC Rf=0.30 (5% MeOH/CH$_2$Cl$_2$). $^1$H NMR (500 MHz, CD$_3$OD) δ 7.96 (m, 2H), 7.90 (dd, J=7.93, 2.14, 1H), 7.83 (d, J=1.83, 1H), 7.72 (dd, J=8.55, 0.92, 1H), 7.54 (d, J=8.55, 1H), 7.51 (d, J=3.36, 1H), 7.48 (d, J=7.93, 1H), 7.34-7.27 (overlapping m, 4H), 6.55 (dd, J=3.36, 0.92, 1H), 2.96 (s, 3H), 2.29 (s, 3H), 1.69 (m, 2H), 1.38 (m, 2H). LC/MS were performed by using Shimadzu-VP instrument with UV detection at 220 nm and Waters Micromass. HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Stop time=3 min, Flow Rate=5 ml/min, Column: Phenomenex-Luna, 3.0×50 mm, S10; (ES+) m/z (M+H)$^+$=577.19, HPLC R$_t$=1.433 min. Analytical HPLC were performed by using Shimadzu-VP instrument with UV detection at 220 nm and 254 nm. Analytical HPLC method: Solvent A=5% MeCN-95% H$_2$O-0.1% TFA, Solvent B=95% MeCN-5% H$_2$O-0.1% TFA, Start % B=20, Final % B=100, Gradient time=15 min, Stop time=18 min, Flow Rate=1 ml/min, Column: Sunfire C18, 3.5 um, 4.6×150 mm, R$_t$=7.74 min; Column: Xbridge Phenyl 3.5 um, 4.6×150 mm, R$_t$=8.42 min. Analytical HPLC method: Solvent A=5% MeOH-95% H$_2$O-10 mM NH$_4$HCO$_3$, Solvent B=95% MeOH-5% H$_2$O-10 mM NH$_4$HCO$_3$, Start % B=50, Final % B=100, Gradient time=15 min, Stop time=18 min, Flow Rate=1 ml/min, Column: Xbridge Phenyl 3.5 um, 4.6×150 mm, R$_t$=9.87 min. tert-butyl 1-(1,6-naphthyridin-2-yl)cyclopropylcarbamate was synthesized in a similar fashion then converted to 1-(1,6-naphthyridin-2-yl)cyclopropanamine using the following approach.

tert-butyl 1-(1,6-naphthyridin-2-yl)cyclopropylcarbamate. Light yellow solid, 59.4% yield. $^1$H NMR (400 MHz, CD$_3$OD) δ ppm 1.35 (br. s., 2 H), 1.44 (m, 2 H), 1.53 (m, 7 H), 1.87 (m, 2 H), 7.85 (m, 2 H), 8.46 (d, J=9 Hz, 1 H), 8.64 (d, J=6 Hz, 1H), 9.26 (s, 1H). LCMS retention time (rt)=2.415 min, m/z 286.2 (M+H) & m/z 284.3 (M−H). HPLC rt=5.126 min. (Sunfire C18), 100% purity and 10.336 min. (Gemini C18), 100% purity. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/10 mM ammonium acetate/10% HPLC grade water), (A=90% HPLC grade water/10 mM ammonium acetate/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

1-(1,6-naphthyridin-2-yl)cyclopropanamine. To a 250 mL RBF was added tert-butyl 1-(1,6-naphthyridin-2-yl)cyclopropylcarbamate (770.5 mg, 2.70 mmol) in 30 mL of DCM along with Hunig's Base (1.2 mL, 6.75 mmol) under a nitrogen atmosphere. The mixture was cooled to 0° C. in an ice bath. To the cold mixture was added drop wise TMS-triflate (975 μl, 5.40 mmol) and the mixture was stirred for 1 hour then allowed to reach room temperature. The mixture was re-cooled to 0° C., and the reaction quenched with 30 mL of saturated sodium bicarbonate. The mixture was diluted with 75 mL of diethyl ether, extracted, washed with brine, dried over sodium sulfate, decanted and evaporated to dryness. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% TFA with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. Yellow solid, 75% yield. $^1$H NMR (400 MHz, CD$_3$OD) δ ppm 1.36 (m, 2H), 1.57 (m, 2 H), 7.78 (d, J=8.78 Hz, 1 H), 7.92 (d, J=6.02 Hz, 1 H), 8.47 (d, J=8.78 Hz, 1 H), 8.67 (d, J=6.02 Hz, 1 H), 9.27 (s, 1 H). LCMS rt=0.415 min., m/z 186.1 (M+H), 98.2% purity.

tert-butyl 1-(1,5-naphthyridin-2-yl)cyclopropylcarbamate was synthesized in a similar fashion then converted to 1-(1,5-naphthyridin-2-yl)cyclopropanamine using the following approach.

tert-butyl 1-(1,5-naphthyridin-2-yl)cyclopropylcarbamate. LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade methanol/0.1% trifluoroacetic acid/10% HPLC grade water), (A=90% HPLC grade water/0.1% trifluoroacetic acid/10% HPLC grade methanol), in 4 minutes with a 1 minute hold at a rate of 0.8 mL/minute. HPLC purity was determined using a Shimadzu analytical LC at 254 nm and 256 nm with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. Yellow solid, 71% yield. $^1$H NMR (400 MHz, CD$_3$OD) δ ppm 1.39 (m, 2 H), 1.55 (m, 2 H), 7.78 (ddd, J=8.78, 2.13, 1.88 Hz, 2 H), 8.36 (d, J=9.03 Hz, 1 H), 8.44 (d, J=8.03 Hz, 1 H), 8.91 (dd, J=4.27, 1.51 Hz, 1 H). LCMS rt=1.868 min, m/z 286.2 (M+H). HPLC rt=10.316 min. (Gemini C18), 98.7% purity.

1-(1,5-naphthyridin-2-yl)cyclopropanamine. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. Tan solid, 67% yield. $^1$H NMR (400 MHz, CD$_3$OD) δ ppm 1.39 (m, 2 H), 1.55 (m, 2 H), 7.78 (ddd, J=8.78, 2.13, 1.88 Hz, 2 H), 8.36 (d, J=9.03 Hz, 1 H), 8.44 (d, J=8.03 Hz, 1 H), 8.91 (dd, J=4.27, 1.51 Hz, 1 H). LCMS rt=0.505 min., m/z 186.1 (M+H), 99.1% purity.

tert-butyl 1-(pyrido[4,3-d]pyrimidin-2-yl)cyclopropylcarbamate. To a microwave vial was added 4-aminonicotinaldehyde (500 mg, 4.09 mmol), tert-butyl 1-carbamimidoylcyclopropylcarbamate, HCl (965 mg, 4.09 mmol), N-ethyl-N-isopropylpropan-2-amine (1.426 mL, 8.19 mmol) and 15 mL of ethanol. The vessel was sealed and the mixture subjected to microwave heating (110° C.) for 8 hours. The crude reaction mixture was purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Phenomenex Luna 10 μm C18 30×100 mm column at a gradient of 0-100% B and a flow rate of 30 mL/min. over 8 minutes with a 4 minute hold. Upon solvent evaporation, 837 mgs (64% yield) of tert-butyl 1-(pyrido[4,3-d]pyrimidin-2-yl)cyclopropylcarbamate was obtained as a tan solid. $^1$H NMR (400 MHz, CD$_3$OD) δ ppm 1.28 (br. s., 1 H), 1.45 (m, 2 H), 1.51 (br. s., 8 H), 1.82 (m, 2 H), 7.78 (d, J=6.02 Hz, 1 H), 8.80 (d, J=6.02 Hz, 1 H), 9.37 (s, 1 H), 9.57 (s, 1H). LCMS rt=1.560 min., m/z 287.31 (M+H), 97.1% purity. HPLC rt=3.968 min. (Sunfire C18), 99.3% purity and 9.326 min. (Gemini C18), 97.5% purity. The LC/MS data was obtained on a Shimadzu analytical LC/Micromass Platform LC (ESI+/−) at 220 nm using the following set of conditions: Phenomenex Luna 3 mm C18, 2×50 mm column, with a gradient of 0-100% B (B=95% HPLC grade acetonitrile/10 mM ammonium acetate/5% HPLC grade water), (A=95% HPLC grade water/10 mM ammonium acetate/5% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

tert-Butyl 1-(pyrido[3,4-d]pyrimidin-2-yl)cyclopropylcarbamate was synthesized and analyzed in an analogous fashion.

tert-butyl 1-(pyrido[3,4-d]pyrimidin-2-yl)cyclopropylcarbamate. Tan solid, 61% yield. $^1$H NMR (400 MHz, CD$_3$OD) δ ppm 1.35 (br. s., 1 H), 1.49 (m, 2 H), 1.55 (br. s., 8 H), 1.85 (m, 2 H), 8.00 (d, J=5.52 Hz, 1 H), 8.71 (d, J=5.52 Hz, 1 H), 9.36 (s, 1 H), 9.59 (s, 1 H). LCMS rt=2.332 min., m/z 287.3 (M+H), 94.8% purity.

1-(pyrido[4,3-d]pyrimidin-2-yl)cyclopropanamine, 2 HCl. To a 25 mL RBF at 0° C., under a nitrogen atmosphere, was added tert-butyl 1-(pyrido[4,3-d]pyrimidin-2-yl)cyclopropylcarbamate (60 mg, 0.210 mmol), dioxane (5 mL) and a 4M solution of hydrochloric acid (0.524 mL, 2.095 mmol) in dioxane. The solution was stirred for 5 minutes at 0° C. then allowed to warm to room temperature and stirred for 3 hrs. Volatiles were removed en vacuo to give 54 mgs (98% yield) of 1-(pyrido[4,3-d]pyrimidin-2-yl)cyclopropanamine, 2 HCl as a light yellow solid. The LC/MS data was obtained on a Shimadzu analytical LCMS (ESI+/−) at 220 nm using the following set of conditions: Phenomenex Luna 3 μm C18, 2×50 mm column, with a gradient of 0-100% B (B=95% HPLC grade methanol/10 mM ammonium acetate/5% HPLC grade water), (A=95% HPLC grade water/10 mM ammonium acetate/5% HPLC grade methanol), in 4 minutes with a 1 minute hold at a rate of 0.8 mL/minute. LCMS rt=1.911 min., m/z 187.1 (M+H), 90% purity.

1-(pyrido[3,4-d]pyrimidin-2-yl)cyclopropanamine, 2 HCl. To a 25 mL RBF at 0° C., under a nitrogen atmosphere, was added tert-butyl 1-(pyrido[3,4-d]pyrimidin-2-yl)cyclopropylcarbamate (60 mg, 0.210 mmol), dioxane (5 mL) and a 4M solution of hydrochloric acid (0.524 mL, 2.095 mmol) in dioxane. The solution was stirred for 5 minutes at 0° C. then allowed to warm to room temperature and stirred for 3 hrs. Volatiles were removed en vacuo to give 54 mgs (98% yield) of 1-(pyrido[3,4-d]pyrimidin-2-yl)cyclopropanamine, 2 HCl as a yellow solid. The LC/MS data was obtained on a Shimadzu analytical LC/Micromass Platform LC (ESI+/−) at 220 nm using the following set of conditions: Phenomenex Luna 3 μm C18, 2×50 mm column, with a gradient of 0-100% B (B=95% HPLC grade acetonitrile/10 mM ammonium acetate/5% HPLC grade water), (A=95% HPLC grade water/10 mM ammonium acetate/5% HPLC grade acetonitrile), in 4 minutes with a 1 minute hold at a rate of 0.8 mL/minute. LCMS rt=2.317 min., m/z 187.1 (M+H), 90% purity.

The bicyclic oxazolopyridine intermediate was made in a similar manner.

tert-butyl 1-(4-hydroxypyridin-3-ylcarbamoyl)cyclopropylcarbamate. To a large screw cap vial was added 3-aminopyridin-4-ol (0.440 g, 4.0 mmol) in DMF (10 mL) along with triethylamine (1.561 mL, 11.2 mmol), 1-(tert-butoxycarbonylamino)cyclopropanecarboxylic acid (0.845 g, 4.2 mmol) and finally TBTU, o-Benzotriazol-1-yl-N,N,N',N'-tetramethyluronium tetrafluoroborate (1.605 g, 5.0 mmol). The vial was sealed and the brown mixture was shaken for 24 hours at room temperature. The reaction mixture was concentrated to an oil, taken up in acetonitrile and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Phenomenex-Luna 10 μm C18 30×100 mm column at a gradient of 0-100% B and a flow rate of 30 mL/min. over 10 minutes with a 5 minute hold. Solvent was removed giving 1.0 gram (81% yield) of tert-butyl 1-(4-hydroxypyridin-3-ylcarbamoyl)cyclopropyl carbamate as a light yellow solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, CD$_3$OD) δ ppm 1.17 (m, 2 H), 1.51 (s, 9 H), 1.59 (m, 2 H), 6.55 (d, J=7.03 Hz, 1H), 7.74 (dd, J=7.03, 1.51 Hz, 1 H), 7.79 (br. s., 1 H), 8.89 (d, 1 H). LCMS rt=1.682, min., m/z 294.3 (M+H). HPLC rt=5.621 min. (Sunfire C18), 94.9% purity and 7.961 min. (Gemini C18), 100% purity.

tert-butyl 1-(3-hydroxypyridin-4-ylcarbamoyl)cyclopropylcarbamate was synthesized in an analogous fashion. Tan solid, 69% yield. $^1$H NMR (400 MHz, CD$_3$OD) δ ppm 1.19 (m, 2 H), 1.53 (br. s., 9 H), 1.60 (m, 2 H), 7.85 (d, J=5.52 Hz, 1 H), 7.90 (br. s., 1 H), 8.30 (d, J=5.52 Hz, 1 H). LCMS rt=1.557, min., m/z 294.3 (M+H), 91% purity.

tert-butyl 1-(oxazolo[4,5-c]pyridin-2-yl)cyclopropylcarbamate. To a 100 mL RBF was added hexachloroethane (296 mg, 1.250 mmol), DCM (5 mL), triphenyl phosphine (393 mg, 1.500 mmol) and triethylamine (0.558 mL, 4.00 mmol). The mixture was stirred for 5 minutes at room temperature. Neat tert-butyl 1-(4-hydroxypyridin-3-ylcarbamoyl)cyclopropyl carbamate (147 mg, 0.5 mmol) was then added. The solution was stirred for 3 hours at room temperature then further diluted with 20 mL of DCM, washed sequentially with 5 mL of saturated ammonium chloride, 5 mL of saturated sodium bicarbonate, 5 mL of brine. The resulting solution was dried over sodium sulfate, decanted and evaporated to an oil. The crude reaction mixture was taken up in 6 mL of acetonitrile and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Phenomenex-Luna 10 μm C18 30×100 mm column at a gradient of 30-100% B and a flow rate of 30 mL/min. over 10 minutes with a 10 minute hold. Solvent was removed giving 111 mgs (79% yield) of a yellow solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. $^1$H NMR (400 MHz, CD$_3$OD) δ ppm 1.38 (br. s., 2 H), 1.51 (m, 9 H), 1.78 (m, 2 H), 7.70 (d, J=5.52 Hz, 1 H), 8.51 (d, J=5.52 Hz, 1 H), 8.89 (s, 1 H). LCMS rt=1.638 min., m/z 276.3 (M+H), 98.0% purity.

tert-butyl 1-(oxazolo[5,4-d]pyridin-2-yl)cyclopropylcarbamate was synthesized in an analogous fashion. Yellow solid, 50% yield. $^1$H NMR (400 MHz, CD$_3$OD) δ ppm 1.25-1.39 (2 H, m), 1.42-1.57 (9 H, m), 1.72-1.82 (2 H, m), 7.67 (1 H, d, J=5.3 Hz), 8.45 (1 H, d, J=5.5 Hz), 8.83 (1H, s). LCMS rt=2.153 min., m/z 276.2 (M+H). HPLC rt=4.511 min. (Sunfire C18), 95.8% purity and 8.058 min. (Gemini C18), 97.1% purity.

1-(oxazolo[4,5-d]pyridin-2-yl)cyclopropanamine, 2 HCl. To a small RBF was added tert-butyl 1-(oxazolo[4,5-c]pyridin-2-yl)cyclopropylcarbamate (107 mg, 0.389 mmol) in dioxane (3 mL) at room temperature along with a 4M dioxane solution of hydrochloric acid (0.972 mL, 3.89 mmol). The mixture was stirred for 3 hours. Volatiles were removed giving 108 mgs (95% yield) of 1-(oxazolo[4,5-c]pyridin-2-yl)cyclopropanamine, 2 HCl as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. $^1$H NMR (400 MHz, CD$_3$OD) δ ppm 1.94 (m, 2 H), 2.07 (m, 2 H), 8.43 (d, J=6.53 Hz, 1 H), 8.96 (d, J=6.53 Hz, 1 H), 9.55 (s, 1 H). LCMS rt=0.288 min., m/z 176.1 (M+H), 86% purity. 1-(oxazolo[5,4-c]pyridin-2-yl)cyclopropanamine, 2 HCl. White solid, 95% yield. LCMS rt=0.295 min., m/z 176.1 (M+H), 84% purity.

(R)-1-(oxazolo[4,5-c]pyridin-2-yl)ethanamine and (S)-1-(oxazolo[4,5-c]pyridin-2-yl)ethanamine were synthesized in a similar fashion.

(S)-1-(oxazolo[4,5-c]pyridin-2-yl)ethanamine, 2HCl. Yellow solid, 68% yield. LCMS rt=0.262, m/z 164.17 (M+H), 60% purity.

(R)-1-(oxazolo[4,5-c]pyridin-2-yl)ethanamine, 2-methanesulfonic acid salt. Tan solid, 98% yield. $^1$H NMR (400 MHz, CD$_3$OD) δ ppm 1.44 (d, J=7.03 Hz, 3 H), 4.18 (d, J=7.03 Hz, 1 H), 7.21 (d, J=6.53 Hz, 1 H), 8.21 (dd, J=6.65, 1.13 Hz, 1 H), 9.26 (d, J=1.00 Hz, 1 H). LCMS rt=0290 min., m/z 164.1 (M+H), 98% purity.

1-(1H-imidazo[4,5-c]pyridin-2-yl)cyclopropanamine was synthesized using the following approach.

1-(Benzyloxycarbonylamino)cyclopropanecarboxylic acid. To a solution of N-(Benzyloxycarbonyloxy)succinimide (1.80 g, 7.23 mmol) in THF (9 mL) was added 1-aminocyclopropanecarboxylic acid, HCl (722 mg, 5.24 mmol) in water (1.4 mL). The mixture was cooled to 0° C. and shaken for 5 minutes. To this mixture was added at 0° C. an aqueous solution of sodium bicarbonate (2.46 g, 29.3 mmol) in 5 mL of water. The mixture was allowed to warm to room temperature and shaken overnight. The product mixture was filtered and the solids set aside. Volatiles were evaporated to near dryness then the crude mixture was diluted with 10 mL of water and 40 mL of DCM. The mixture was extracted and the DCM layer was set aside. The resulting aqueous layer was cooled in an ice bath then acidified with 10 mL of acetic acid. The solid was filtered, washed with 1 mL of water ×2 then dried under vacuum for 2 hours giving 856 mgs of 1-(benzyloxycarbonylamino) cyclopropanecarboxylic acid as a fluffy white solid (63% yield). $^1$H NMR (400 MHz, DMSO-d6) δ ppm 0.93-1.10 (m, 2 H), 1.26-1.37 (m, 2 H), 5.02 (s, 2 H), 7.25-7.44 (m, 5 H), 7.89 (s, 1 H), 12.44 (d, 1 H). LCMS rt=2.112 min., m/z 236.1 (M+H), 90% purity. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute.

Benzyl 1-(4-aminopyridin-3-ylcarbamoyl)cyclopropylcarbamate and benzyl 1-(3-aminopyridin-4-ylcarbamoyl)cyclopropylcarbamate. To a 100 mL RBF was added pyridine-3,4-diamine (327 mg, 3.00 mmol) in DMF (30 mL) along with 1-(benzyloxycarbonylamino)cyclopropanecarboxylic acid (706 mg, 3.00 mmol), triethylamine. (1.20 mL, 8.40 mmol), and TBTU, 2-(1H-benzo[d][1,2,3]triazol-1-yl)-1,1,3,3-tetramethylisouronium tetrafluoroborate (1.20 mg, 3.75 mmol). The mixture was stirred overnight at room temperature. The reaction mixture was diluted with 50 mL of DCM and extracted; the organics were washed with 10 mL of water, 10 mL of brine, dried over magnesium sulfate, decanted and evaporated to dryness to give 949 mgs of a mixture of benzyl 1-(4-aminopyridin-3-ylcarbamoyl)cyclopropylcarbamate and benzyl 1-(3-aminopyridin-4-ylcarbamoyl)cyclopropylcarbamate as a yellow solid (68% yield). $^1$H NMR (400 MHz, CD$_3$OD) δ ppm 1.12-1.19 (m, 2 H), 1.52-1.60 (m, 2 H), 5.13 (s, 2 H), 7.23-7.43 (m, 6 H), 7.82 (d, J=5.5 Hz, 1 H), 8.06 (s, 1 H). LCMS rt=1.880 min., m/z 327.1 (M+H), 71% purity.

Benzyl 1-(1H-imidazo[4,5-e]pyridin-2-yl)cyclopropylcarbamate. To a medium size microwave vial was added 5 mL of acetic acid and 850 mgs of the crude reaction mixture prepared in the previous step (benzyl 1-(4-aminopyridin-3-lcarbamoyl)cyclopropylcarbamate and benzyl 1-(3-aminopyridin-4-ylcarbamoyl)cyclopropylcarbamate). The vial was sealed and the mixture heated at 120° C. for 70 minutes in the microwave. The vessel was cooled to near 0° C. and 50 mL of cold saturated sodium carbonate was added along with 100 mL of 10:1 DCM/methanol. The product was extracted; the organics washed with brine, dried over magnesium sulfate and evaporated. The product mixture was taken up in 15 mL of methanol and purified using a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Phenomenex-Luna 10 μm C18 30×100 mm column at a gradient of 0-100% B and a flow rate of 40 mL/min. over 15 minutes with a 10 minute hold. Solvent was removed giving a 70% yield of benzyl 1-(1H-imidazo[4,5-c]pyridin-2-yl)cyclopropylcarbamate as a light yellow solid. $^1$H NMR (400 MHz, CD$_3$OD) δ ppm 1.44-1.59 (m, 2 H), 1.68-1.83 (m, 2 H), 5.05-5.14 (m, 2 H), 6.99-7.14 (m, 1 H), 7.19-7.41 (m, 4 H), 7.88-7.97 (m, 1 H), 8.40 (d, J=6.5 Hz, 1 H), 8.97 (s, 1H). LCMS rt=1.483 min., m/z 309.2 (M+H), 94.5% purity.

1-(1H-imidazo[4,5-e]pyridin-2-yl)cyclopropanamine. To a small RBF was added benzyl 1-(1H-imidazo[4,5-c]pyridin-2-yl)cyclopropylcarbamate (939 mg, 3.05 mmol) in methanol (13 ml). The flask was sealed with a septa and the solution was degassed and flushed with nitrogen several times. To the solution was then added 10% Palladium(II) on carbon (97 mg, 91 μmol), and a balloon of hydrogen was added to the top of the flask. The mixture was stirred overnight at room temperature. The mixture was pushed through a plug of celite in a Whatman Autovial (equipped with a 0.45 uM nylon membrane and a glass microfiber prefilter). Volatiles were removed giving 640 mgs (100% yield) of 1-(1H-imidazo[4,5-c]pyridin-2-yl)cyclopropanamine as a yellow solid. $^1$H NMR (400 MHz, CD$_3$OD) δ ppm 1.67-1.72 (m, 2 H), 1.73- 1.80 (m, 2 H), 7.92 (m, 1 H), 8.40 (d, J=7.0 Hz, 1 H), 9.05 (s, 1 H). LCMS rt=0.293 min., m/z 175.1 (M+H), 90.7% purity.

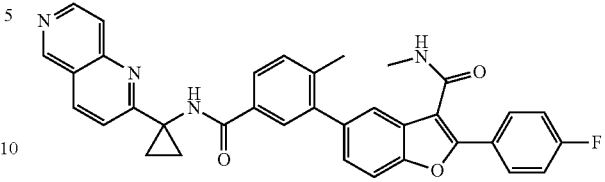

5-(5-(1-(1,6-naphthyridin-2-yl)cyclopropylcarbamoyl)-2-methylphenyl)-2-(4-fluorophenyl)-N-methylbenzofuran-3-carboxamide. Yellow solid, 43% yield. $^1$H NMR (400 MHz, THF-d8) δ ppm 1.43 (m, 2 H), 1.89 (m, 2 H), 2.32 (s, 3 H), 2.89 (d, J=4.77 Hz, 3 H), 7.23 (m, 2 H), 7.33 (dd, J=8.53, 1.76 Hz, 1 H), 7.39 (d, J=8.53 Hz, 1 H), 7.44 (d, J=4.27 Hz, 1 H), 7.60 (d, J=8.53 Hz, 1 H), 7.66 (d, J=5.77 Hz, 1 H), 7.71 (d, J=1.25 Hz, 1 H), 7.73 (d, J=8.78 Hz, 1 H), 7.89 (m, 2 H), 8.11 (m, 2 H), 8.21 (d, J=8.78 Hz, 1 H), 8.59 (d, J=5.77 Hz, 2 H), 9.14 (s, 1H). LCMS rt=2.626 min., m/z 571.2 (M+H). HPLC rt=7.391 min. (Sunfire C18), 100% purity and 11.914 min. (Gemini C18), 99.9% purity.

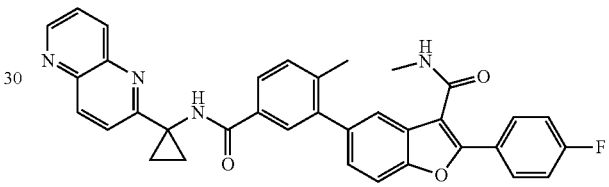

5-(5-(1-(1,5-naphthyridin-2-yl)cyclopropylcarbamoyl)-2-methylphenyl)-2-(4-fluorophenyl)-N-methylbenzofuran-3-carboxamide. Yellow solid, 43% yield. $^1$H NMR (400 MHz, THF-d8) δ ppm 1.40 (m, 2 H), 1.86 (m, 2 H), 2.31 (s, 3 H), 2.89 (d, J=4.52 Hz, 3 H), 7.22 (m, 2 H), 7.32 (dd, J=8.53, 1.76 Hz, 1 H), 7.37 (d, J=8.78 Hz, 1 H), 7.48 (d, J=4.02 Hz, 1 H), 7.57 (m, 2 H), 7.71 (d, J=1.25 Hz, 1 H), 7.82 (d, J=8.78 Hz, 1 H), 7.89 (m, 2 H), 8.11 (m, 2 H), 8.18 (m, 2 H), 8.64 (s, 1 H), 8.80 (d, J=2.76 Hz, 1 H). LCMS rt=4.233 min., m/z 571.5 (M+H). HPLC rt=8.111 min. (Sunfire C18), 98.1% purity and 12.031 min. (Gemini C18), 98.1% purity.

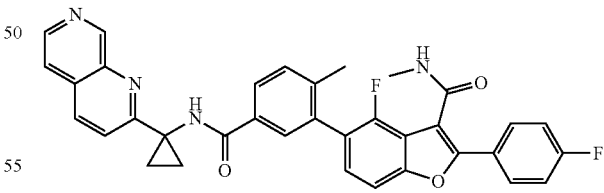

5-(5-(1-(1,7-naphthyridin-2-yl)cyclopropylcarbamoyl)-2-methylphenyl)-4-fluoro-2-(4-fluoro phenyl)-N-methylbenzofuran-3-carboxamide. Yellow solid, 20% yield. $^1$H NMR (400 MHz, THF-d8) δ ppm 1.41 (q, J=4.18 Hz, 2 H), 1.88 (q, J=4.10 Hz, 2 H), 2.26 (s, 3 H), 2.88 (d, J=4.77 Hz, 3 H), 7.23 (m, 3 H), 7.41 (d, J=8.03 Hz, 1 H), 7.46 (d, J=8.53 Hz, 1 H), 7.61 (d, J=5.52 Hz, 1 H), 7.69 (d, J=4.27 Hz, 1 H), 7.81 (d, J=8.53 Hz, 1 H), 7.85 (d, J=1.76 Hz, 1 H), 7.91 (dd, J=7.91, 1.88 Hz, 1 H), 8.07 (m, 3 H), 8.44 (d, J=5.52 Hz, 1 H), 8.61 (s, 1 H), 9.21 (s, 1 H). LCMS rt=2.543 min., m/z 589.2 (M+H).

HPLC rt=7.126 min. (Sunfire C18), 100% purity and 11.469 min. (Gemini C18), 100% purity.

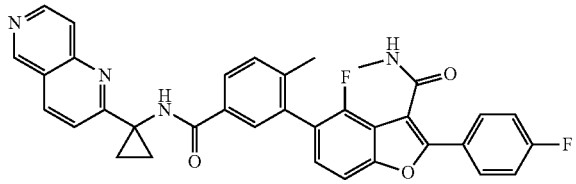 [SMILES: CNC(=O)c1c(-c2ccc(F)cc2)oc2ccc(-c3cc(C(=O)NC4(c5ccc6cnccc6n5)CC4)ccc3C)c(F)c12]

5-(5-(1-(1,6-naphthyridin-2-yl)cyclopropylcarbamoyl)-2-methylphenyl)-4-fluoro-2-(4-fluoro phenyl)-N-methylbenzofuran-3-carboxamide. Yellow solid, 34% yield. $^1$H NMR (400 MHz, THF-d8) δ ppm 1.42 (q, J=4.02 Hz, 2 H), 1.89 (m, 2 H), 2.26 (s, 3 H), 2.88 (d, J=4.77 Hz, 3 H), 7.24 (m, 3 H), 7.41 (d, J=7.78 Hz, 1 H), 7.47 (d, J=8.53 Hz, 1 H), 7.67 (m, 2 H), 7.73 (d, J=8.53 Hz, 1 H), 7.85 (d, J=1.76 Hz, 1H), 7.92 (dd, J=8.03, 1.76 Hz, 1 H), 8.07 (m, 2 H), 8.21 (d, J=8.78 Hz, 1 H), 8.59 (d, J=5.77 Hz, 2 H), 9.14 (s, 1 H). LCMS rt=2.555 min., m/z 589.2 (M+H). HPLC rt=7.098 min. (Sunfire C18), 98.9% purity and 11.484 min. (Gemini C18), 100% purity.

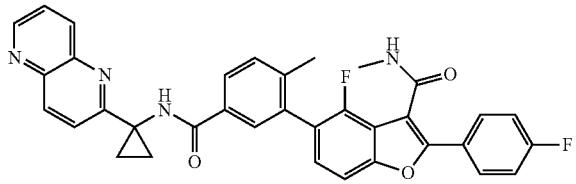

5-(5-(1-(1,5-naphthyridin-2-yl)cyclopropylcarbamoyl)-2-methylphenyl)-4-fluoro-2-(4-fluoro phenyl)-N-methylbenzofuran-3-carboxamide. Yellow solid, 42% yield. $^1$H NMR (400 MHz, THF-d8) δ ppm 1.40 (m, 2 H), 1.85 (m, 2 H), 2.26 (s, 3 H), 2.88 (d, J=4.77 Hz, 3 H), 7.24 (m, 3 H), 7.40 (d, J=8.03 Hz, 1 H), 7.46 (d, J=8.28 Hz, 1 H), 7.55 (dd, J=8.53, 4.02 Hz, 1 H), 7.72 (d, J=4.27 Hz, 1 H), 7.82 (d, J=9.03 Hz, 1 H), 7.86 (d, J=1.76 Hz, 1 H), 7.92 (dd, J=7.91, 1.88 Hz, 1 H), 8.07 (m, 2 H), 8.17 (m, 2 H), 8.64 (s, 1 H), 8.80 (dd, 1 H). LCMS rt=3.385 min., m/z 589.3 (M+H). HPLC rt=7.743 min. (Sunfire C18), 98.1% purity and 11.546 min. (Gemini C18), 98.1% purity.

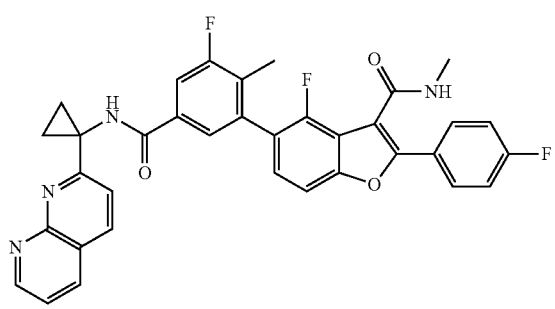 [SMILES: CNC(=O)c1c(-c2ccc(F)cc2)oc2ccc(-c3cc(C(=O)NC4(c5ccc6cccnc6n5)CC4)cc(F)c3C)c(F)c12]

5-(5-(1-(1,8-naphthyridin-2-yl)cyclopropylcarbamoyl)-3-fluoro-2-methylphenyl)-4-fluoro-2-(4-fluorophenyl)-N-methylbenzofuran-3-carboxamide. To a 1 dram vial was added DMF (1.3 ml), 1-(1,8-naphthyridin-2-yl)cyclopropanamine, 2 HCl (38.7 mg, 0.150 mmol), N-ethyl-N-isopropylpropan-2-amine (87 μl, 0.500 mmol), 3-fluoro-5-(4-fluoro-2-(4-fluorophenyl)-3-(methylcarbamoyl)benzofuran-5-yl)-4-methylbenzoic acid (43.9 mg, 0.1 mmol) and finally HATU, 2-(3H-[1,2,3]triazolo[4,5-b]pyridin-3-yl)-1,1,3,3-tetramethylisouronium hexafluorophosphate(V) (152 mg, 0.400 mmol). The vial was capped and shaken overnight. The crude product was purified using a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Phenomenex Luna 10 μm C18 30×100 mm column at a gradient of 40-100% B and a flow rate of 40 mL/min. over 12 minutes with a 13 minute hold. The solvent was removed giving 33.3 mgs (54% yield) of 5-(5-(1-(1,8-naphthyridin-2-yl)cyclopropylcarbamoyl)-3-fluoro-2-methylphenyl)-4-fluoro-2-(4-fluorophenyl)-N-methylbenzofuran-3-carboxamide as a light yellow solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Xbridge Phenyl C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.42 (m, 2 H), 1.93 (m, 2 H), 2.17 (d, J=1.00 Hz, 3 H), 2.90 (m, 3 H), 7.23 (m, 3 H), 7.37 (dd, J=8.03, 4.27 Hz, 1 H), 7.44 (d, J=8.28 Hz, 1 H), 7.65 (d, J=8.28 Hz, 1 H), 7.75 (m, 3 H), 8.08 (m, 3 H), 8.18 (dd, J=8.03, 2.01 Hz, 1 H), 8.84 (s, 1 H), 8.93 (dd, J=4.02, 1.76 Hz, 1 H). LCMS rt=2.595 min., m/z 607.3 (M+H), 99.5% purity. HPLC rt=7.160 min. (Sunfire C18), 98.7% purity and 11.701 min(Gemini C18), 99.2% purity.

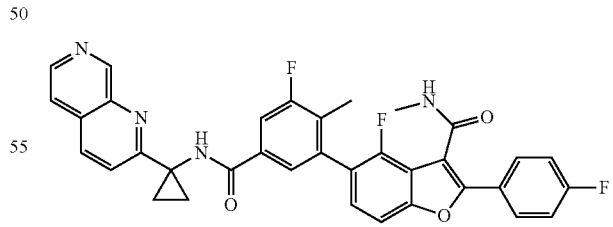

5-(5-(1-(1,7-naphthyridin-2-yl)cyclopropylcarbamoyl)-3-fluoro-2-methylphenyl)-4-fluoro-2-(4-fluorophenyl)-N-methylbenzofuran-3-carboxamide. Yellow solid, 46% yield. $^1$H NMR (400 MHz, THF-d8) δ ppm 1.42 (m, 2 H), 1.88 (m, 2 H), 2.18 (d, J=1.51 Hz, 3 H), 2.88 (d, J=4.77 Hz, 3 H), 7.25 (m, 3 H), 7.49 (d, J=8.53 Hz, 1 H), 7.62 (d, J=5.52 Hz, 1 H), 7.73 (m, 3 H), 7.79 (d, J=8.78 Hz, 1 H), 8.07 (m, 3 H), 8.45 (d, J=5.52 Hz, 1 H), 8.71 (s, 1 H), 9.21 (s, 1 H). LCMS rt=2.626 min., m/z 607.3 (M+H), 96.1% purity. HPLC rt=7.348 min. (Sunfire C18), 98.6% purity and 11.881 min. (Gemini C18), 97.9% purity.

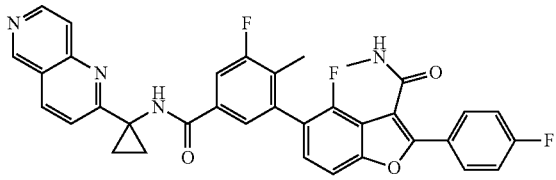 [SMILES: CNC(=O)c1c(-c2ccc(F)cc2)oc2ccc(-c3cc(C(=O)NC4(c5ccc6cnccc6n5)CC4)cc(F)c3C)c(F)c12]

5-(5-(1-(1,6-naphthyridin-2-yl)cyclopropylcarbamoyl)-3-fluoro-2-methylphenyl)-4-fluoro-2-(4-fluorophenyl)-N-methylbenzofuran-3-carboxamide. Orange solid, 77% yield. ¹H NMR (400 MHz, THF-d8) δ ppm 1.43 (m, 2 H), 1.89 (q, J=4.10 Hz, 2 H), 2.18 (d, J=1.25 Hz, 3 H), 2.89 (d, J=4.77 Hz, 3 H), 7.25 (m, 3 H), 7.49 (d, J=8.53 Hz, 1 H), 7.70 (m, 5 H), 8.07 (m, 2 H), 8.22 (d, J=8.53 Hz, 1 H), 8.60 (d, J=5.77 Hz, 1 H), 8.69 (s, 1 H), 9.15 (s, 1 H). LCMS rt=2.625 min., m/z 607.3 (M+H), 96.4% purity. HPLC rt=7.358 min. (Sunfire C18), 100% purity and 11.869 min. (Gemini C18), 98.2% purity.

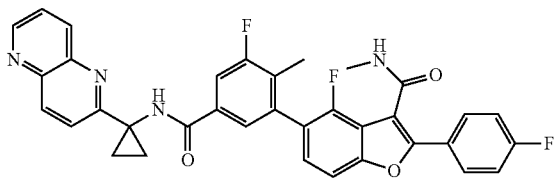 [SMILES: CNC(=O)c1c(-c2ccc(F)cc2)oc2ccc(-c3cc(C(=O)NC4(c5ccc6ncccc6n5)CC4)cc(F)c3C)c(F)c12]

5-(5-(1-(1,5-naphthyridin-2-yl)cyclopropylcarbamoyl)-3-fluoro-2-methylphenyl)-4-fluoro-2-(4-fluorophenyl)-N-methylbenzofuran-3-carboxamide. Orange solid, 76% yield. ¹H NMR (400 MHz, THF-d8) δ ppm 1.40 (m, 2 H), 1.84 (m, 2 H), 2.17 (s, 3 H), 2.88 (d, J=4.77 Hz, 3 H), 7.24 (m, 3 H), 7.46 (d, J=8.28 Hz, 1H), 7.55 (dd, J=8.53, 4.02 Hz, 1 H), 7.77 (m, 4 H), 8.05 (m, 2 H), 8.17 (m, 2 H), 8.79 (d, J=4.27, 2.76 Hz, 2 H). LCMS rt=3.588 min., m/z 607.3 (M+H), 98.8% purity. HPLC rt=8.284 min. (Sunfire C18), 97.6% purity and 11.793 min. (Gemini C18), 98.4% purity.

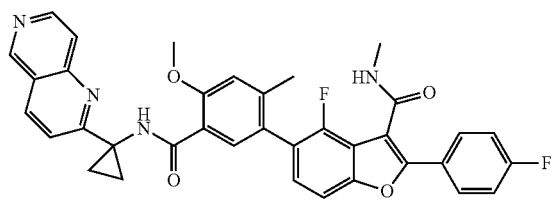 [SMILES: CNC(=O)c1c(-c2ccc(F)cc2)oc2ccc(-c3cc(C(=O)NC4(c5ccc6cnccc6n5)CC4)c(OC)cc3C)c(F)c12]

5-(5-(1-(1,6-naphthyridin-2-yl)cyclopropylcarbamoyl)-4-methoxy-2-methylphenyl)-4-fluoro-2-(4-fluorophenyl)-N-methylbenzofuran-3-carboxamide. To a 50 mL RBF was added 5-(4-fluoro-2-(4-fluorophenyl)-3-(methylcarbamoyl)benzofuran-5-yl)-2-methoxy-4-methylbenzoic acid (57.0 mg, 0.1263 mmol) in DMF (4 mL) along with Hunig's Base (110 μl, 0.632 mmol), 1-(1,6-naphthyridin-2-yl)cyclopropanamine (37.4 mg, 0.202 mmol) and HATU, O-(7-Azabenzotriazol-1-yl)-N,N,N',N'-tetramethyluronium hexafluorophosphate (192 mg, 0.505 mmol). The vessel was sealed, placed under nitrogen, and stirred overnight at room temperature. The crude product was purified using a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Phenomenex Luna 10 μm C18 30×100 mm column at a gradient of 40-100% B and a flow rate of 40 mL/min. over 12 minutes with a 13 minute hold. The solvent was removed giving 39.1 mgs (40% yield) of 5-(5-(1-(1,6-naphthyridin-2-yl)cyclopropylcarbamoyl)-4-methoxy-2-methylphenyl)-4-fluoro-2-(4-fluorophenyl)-N-methyl Benzofuran-3-carboxamide as a tan solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Xbridge Phenyl C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. ¹H NMR (400 MHz, THF-d8) δ ppm 1.51 (m, 2 H), 1.96 (m, 2 H), 2.27 (s, 3 H), 2.87 (d, J=4.77 Hz, 3 H), 4.07 (s, 3 H), 7.14 (s, 1 H), 7.21 (m, 3 H), 7.44 (d, J=8.53 Hz, 1 H), 7.70 (d, J=4.52 Hz, 1H), 7.91 (m, 3 H), 8.08 (m, 2 H), 8.40 (d, J=8.53 Hz, 1 H), 8.70 (m, 2 H). LCMS rt=2.525 min., m/z 619.4 (M+H), 96.4% purity. HPLC rt=7.201 min. (Sunfire C18), 93.4% purity and 11.724 min. (Gemini C18), 96.3% purity.

5-(5-(1-(1,7-naphthyridin-2-yl)cyclopropylcarbamoyl)-4-methoxy-2-methylphenyl)-4-fluoro-2-(4-fluorophenyl)-N-methylbenzofuran-3-carboxamide. Yellow solid, 82% yield. ¹H NMR (400 MHz, THF-d8) δ ppm 1.43 (m, 2 H), 1.90 (m, 2 H), 2.26 (s, 3 H), 2.87 (d, J=4.77 Hz, 3 H), 4.06 (s, 3 H), 7.12 (s, 1 H), 7.21 (m, 3H), 7.43 (d, J=8.53 Hz, 1 H), 7.62 (d, J=5.52 Hz, 1 H), 7.72 (d, J=4.52 Hz, 1 H), 7.87 (d, J=8.78 Hz, 1 H), 7.94 (s, 1 H), 8.08 (m, 3 H), 8.44 (d, J=5.52 Hz, 1 H), 8.69 (s, 1 H), 9.22 (s, 1 H). LCMS rt=2.412 min., m/z 619.5

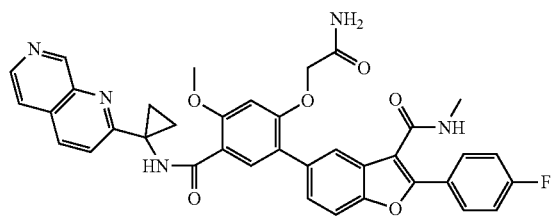 [SMILES: CNC(=O)c1c(-c2ccc(F)cc2)oc2ccc(-c3cc(C(=O)NC4(c5ccc6ccncc6n5)CC4)c(OC)cc3OCC(N)=O)cc12]

5-(5-(1-(1,7-naphthyridin-2-yl)cyclopropylcarbamoyl)-2-(2-amino-2-oxoethoxy)-4-methoxy phenyl)-2-(4-fluorophenyl)-N-methylbenzofuran-3-carboxamide. To a small RBF was added 4-(2-amino-2-oxoethoxy)-5-(2-(4-fluorophenyl)-3-(methylcarbamoyl)benzofuran-5-yl)-2-methoxybenzoic acid (40.5 mg, 0.082 mmol), DMF (3 mL), N-ethyl-N-diisopropylpropan-2-amine (0.086 mL, 0.493 mmol), 1-(1,7-naphthyridin-2-yl)cyclopropanamine, 2 HCl (34.0 mg, 0.132 mmol) and HATU, 2-(3H-[1,2,3]triazolo[4,5-b]pyridin-3-yl)-1,1,3,3-tetramethylisouronium hexafluorophosphate(V) (125 mg, 0.329 mmol). The reaction mixture was stirred over night at room temperature. The crude reaction mixture was then evacuated to near dryness, taken up in 6 mL of methanol and purified using a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Phenomenex-Luna 10 µm C18 30×100 mm column at a gradient of 40-100% B and a flow rate of 40 mL/min. over 12 minutes with a 13 minute hold. Solvent was removed giving 26.1 mgs (46.6% yield) of 5-(5-(1-(1,7-naphthyridin-2-yl)cyclopropylcarbamoyl)-2-(2-amino-2-oxoethoxy)-4-methoxy phenyl)-2-(4-fluorophenyl)-N-methylbenzofuran-3-carboxamide as a yellow solid. The LC/MS data was obtained on a Shimadzu analytical LC/Micromass Platform LC (ESI+) at 220 nm using the following set of conditions: Phenomenex Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 µm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 µm 4.6× 150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, DMF-d7) δ ppm 1.54 (m, 2 H), 1.90 (m, 2 H), 2.96 (d, J=3.51 Hz, 3 H), 4.19 (s, 3 H), 4.81 (s, 2 H), 7.06 (s, 1 H), 7.28 (br. s., 1 H), 7.41 (t, J=8.91 Hz, 2 H), 7.46 (br. s., 1 H), 7.71 (m, 2 H), 7.87 (d, J=5.27 Hz, 1 H), 7.95 (s, 1 H), 8.03 (m, 2 H), 8.11 (dd, J=8.91, 5.40 Hz, 2 H), 8.31 (d, J=4.27 Hz, 1 H), 8.39 (d, J=8.78 Hz, 1 H), 8.57 (d, J=4.52 Hz, 1 H), 9.05 (s, 1 H), 9.28 (br. s., 1 H). LCMS rt=2.097 min., m/z 660.5 (M+H). HPLC rt=6.203 min. (Sunfire C18), 96.8% purity and 10.883 min. (Gemini C18), 96.8% purity.

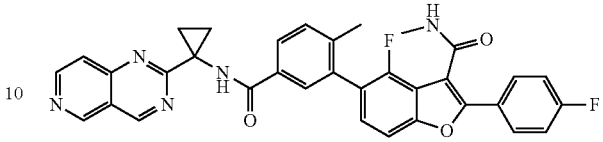

4-fluoro-2-(4-fluorophenyl)-N-methyl-5-(2-methyl-5-(1-(pyrido[4,3-d]pyrimidin-2-yl)cyclo-propylcarbamoyl)phenyl)benzofuran-3-carboxamide, 2 TFA. To a 25 mL RBF flask containing freshly made 1-(pyrido[4,3-d]pyrimidin-2-yl)cyclo propanamine, 2 HCl was added DMF (1.8 mL) and Hunig's Base (122 µl, 0.700 mmol). The mixture was stirred for 5 minutes at room temperature followed by the addition of 3-(4-fluoro-2-(4-fluorophenyl)-3-(methylcarbamoyl)benzofuran-5-yl)-4-methylbenzoic acid (29.5 mg, 0.07 mmol) in DMF (1.8 mL) along with HATU (106 mg, 0.280 mmol). The reaction was stirred overnight at room temperature. The crude product mixture was evaporated to a tan oil, diluted with methanol and purified using a Shimadzu preparative HPLC employing methanol/water/trifluoroacetic acid where solvent A was 10% methanol/90% water/0.1% trifluoroacetic acid and solvent B was 10% water/90% methanol/0.1% trifluoroacetic acid with a Phenomenex-Luna 10 µm C18 30×100 mm column at a gradient of 40-100% B and a flow rate of 40 mL/min. over 15 minutes with a 10 minute hold. Solvent was removed giving 14.2 mgs (24% yield) of 4-fluoro-2-(4-fluorophenyl)-N-methyl-5-(2-methyl-5-(1-(pyrido[4,3-d]pyrimidin-2-yl)cyclo-propylcarbamoyl)phenyl)benzofuran-3-carboxamide, 2 TFA as a yellow solid. The LC/MS data was obtained on a Shimadzu analytical LC/Micromass Platform LC (ESI+) at 220 nm using the following set of conditions: Phenomenex Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 µm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 µm 4.6× 150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.24 (m, 2 H), 1.65 (m, 2 H), 2.27 (s, 3 H), 2.88 (d, J=4.77 Hz, 3 H), 7.26 (m, 2 H), 7.39 (m, 1 H), 7.46 (m, 2 H), 7.54 (m, 1 H), 7.67 (m, 2 H), 7.86 (d, J=1.76 Hz, 1 H), 7.94 (dd, J=7.91, 1.88 Hz, 1 H), 8.07 (m, 2 H), 8.61 (d, J=7.03 Hz, 1 H), 8.68 (m, 1 H), 9.88 (s, 1H).

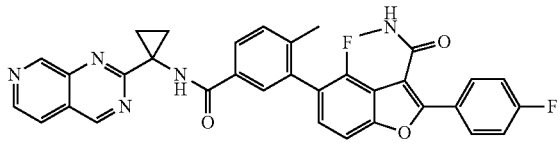 [SMILES: CNC(=O)c1c(-c2ccc(F)cc2)oc2ccc(-c3cc(C(=O)NC4(c5ncc6ccncc6n5)CC4)ccc3C)c(F)c12]

4-fluoro-2-(4-fluorophenyl)-N-methyl-5-(2-methyl-5-(1-(pyrido[3,4-d]pyrimidin-2-yl)cyclopropylcarbamoyl)phenyl)benzofuran-3-carboxamide was synthesized and analyzed in an analogous fashion. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.50 (m, 2 H), 1.83 (m, 2 H), 2.26 (s, 3 H), 2.88 (d, J=4.77 Hz, 3 H), 7.24 (m, 3 H), 7.38 (d, J=8.03 Hz, 1 H), 7.46 (d, J=8.28 Hz, 1 H), 7.71 (d, J=4.27 Hz, 1 H), 7.77 (m, 1 H), 7.85 (d, J=1.51 Hz, 1 H), 7.91 (dd, J=7.91, 1.88 Hz, 1 H), 8.08 (m, 2 H), 8.54 (s, 1 H), 8.60 (d, J=5.52 Hz, 1 H), 9.23 (s, 1 H), 9.41 (s, 1 H). LCMS rt=2.497 min., m/z 590.4 (M+H). HPLC rt=7.205 min. (Sunfire C18), 99.0% purity and 11.124 min. (Gemini C18), 97.2% purity.

LCMS rt=2.325 min., m/z 590.40 (M+H). HPLC rt=6.496 min. (Sunfire C18), 95.1% purity and 11.088 min. (Gemini C18), 95.8% purity.

0.113 mmol), and finally HATU, 2-(3H-[1,2,3]triazolo[4,5-b]pyridin-3-yl)-1,1,3,3-tetramethylisouronium hexafluorophosphate(V) (114 mg, 0.300 mmol). The vial was sealed and the mixture shaken at room temperature overnight. The crude reaction mixture was further diluted with 2 mL of acetonitrile and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters Sunfire 5 μm C18 30×150 mm column at a gradient of 30-100% B and a flow rate of 30 mL/min. over 20 minutes with a 10 minute hold. Solvent was removed giving 6 mgs (13% yield) of 4-fluoro-2-(4-fluorophenyl)-N-methyl-5-(2-methyl-5-(1-(oxazolo[4,5-c]pyridin-2-yl)cyclopropylcarbamoyl)phenyl)benzofuran-3-carboxamide as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (500 MHz, THF-d8) δ ppm 1.50 (m, 2 H), 1.79 (m, 2 H), 2.26 (s, 3 H), 2.89 (m, 3 H), 7.25 (m, 3 H), 7.41 (d, J=8.24 Hz, 1 H), 7.48 (m, 2 H), 7.71 (d, J=4.88 Hz, 1 H), 7.80 (d, J=1.83 Hz, 1 H), 7.87 (dd, J=7.93, 1.83 Hz, 1 H), 8.08 (m, 2 H), 8.41 (d, J=5.49 Hz, 1 H), 8.70 (s, 1 H), 8.80 (s, 1 H). LCMS rt=2.327 min., m/z 579.3 (M+H), 94.5% purity. HPLC rt=6.696 min. (Sunfire C18), 98.0% purity and 10.403 min. (Gemini C18), 98.6% purity.

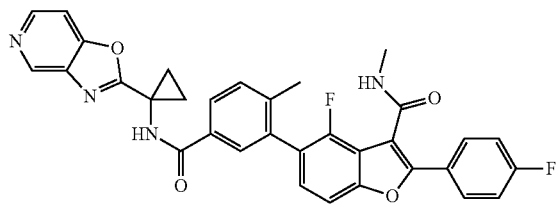 [SMILES: CNC(=O)c1c(-c2ccc(F)cc2)oc2ccc(-c3cc(C(=O)NC4(c5nc6cnccc6o5)CC4)ccc3C)c(F)c12]

4-fluoro-2-(4-fluorophenyl)-N-methyl-5-(2-methyl-5-(1-(oxazolo[4,5-d]pyridin-2-yl)cyclopropyl carbamoyl)phenyl)benzofuran-3-carboxamide. To a screw cap vial was added, at room temperature, 3-(4-fluoro-2-(4-fluorophenyl)-3-(methyl carbamoyl)benzofuran-5-yl)-4-methylbenzoic acid (31.6 mg, 0.075 mmol) in DMF (1.8 mL) along with N-ethyl-N,N-diisopropylpropan-2-amine (79 μl, 0.450 mmol), 1-(oxazolo[4,5-c]pyridin-2-yl)cyclopropanamine, 2 HCl (27.9 mg,

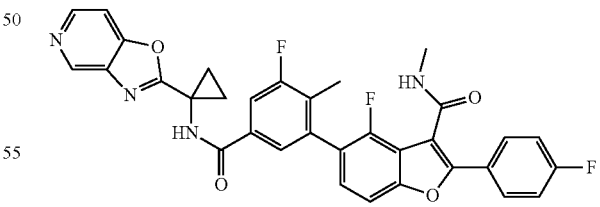

4-fluoro-5-(3-fluoro-2-methyl-5-(1-(oxazolo[4,5-c]pyridin-2-yl)cyclopropylcarbamoyl)phenyl)-2-(4-fluorophenyl)-N-methylbenzofuran-3-carboxamide. To a screw cap vial was added, at room temperature, 3-fluoro-5-(4-fluoro-2-(4-fluorophenyl)-3-(methylcarbamoyl)benzofuran-5-yl)-4-methylbenzoic acid (33.0 mg, 0.075 mmol) in DMF (1.8 mL) along with N-ethyl-N,N-diisopropylpropan-2-amine (79 μl, 0.450 mmol), 1-(oxazolo[4,5-c]pyridin-2-yl)cyclopropan-amine, 2 HCl (27.9 mg, 0.113 mmol), and finally HATU, 2-(3H-[1,2,3]triazolo[4,5-b]pyridin-3-yl)-1,1,3,3-tetramethylisouronium hexafluorophosphate(V) (114 mg, 0.300 mmol). The vial was sealed and the mixture shaken at room temperature overnight. The crude reaction mixture was further diluted with 2 mL of acetonitrile and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters Sunfire 5 μm C18 30×150 mm column at a gradient of 30-100% B and a flow rate of 30 mL/min. over 20 minutes with a 10 minute hold. Solvent was removed giving 10 mgs (21% yield) of 4-fluoro-5-(3-fluoro-2-methyl-5-(1-(oxazolo[4,5-c]pyridin-2-yl)cyclopropylcarbamoyl)phenyl)-2-(4-fluorophenyl)-N-methylbenzofuran-3-carboxamide as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.52 (m, 2 H), 1.79 (m, 2 H), 2.18 (d, J=1.51 Hz, 3 H), 2.89 (d, J=4.77 Hz, 3 H), 7.25 (m, 3 H), 7.48 (m, 2 H), 7.69 (m, 3 H), 8.07 (m, 2 H), 8.41 (d, J=5.52 Hz, 1 H), 8.80 (m, 2 H). LCMS rt=2.407 min., m/z 597.3 (M+H), 94.7% purity. HPLC rt=6.933 min. (Sunfire C18), 97.4% purity and 10.876 min. (Gemini C18), 97.4% purity.

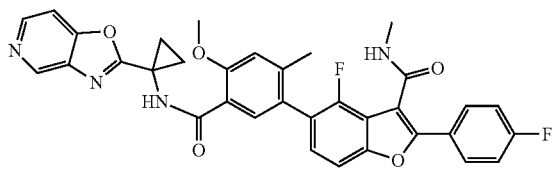 [SMILES: CNC(=O)c1c(-c2ccc(F)cc2)oc2ccc(-c3cc(C(=O)NC4(c5nc6cnccc6o5)CC4)c(OC)cc3C)c(F)c12]

4-fluoro-2-(4-fluorophenyl)-5-(4-methoxy-2-methyl-5-(1-(oxazolo[4,5-d]pyridin-2-yl)cyclopropyl carbamoyl)phenyl)-N-methylbenzofuran-3-carboxamide. To a screw cap vial was added, at room temperature, 5-(4-fluoro-2-(4-fluorophenyl)-3-(methylcarbamoyl)benzofuran-5-yl)-2-methoxy-4-methylbenzoic acid (33.9 mg, 0.075 mmol) in DMF (1.8 mL) along with N-ethyl-N,N-diisopropylpropan-2-amine (79 μl, 0.450 mmol), 1-(oxazolo[4,5-c]pyridin-2-yl)cyclopropanamine, 2 HCl (27.9 mg, 0.113 mmol), and finally HATU, 2-(3H-[1,2,3]triazolo[4,5-b]pyridin-3-yl)-1,1,3,3-tetramethylisouronium hexafluorophosphate(V) (114 mg, 0.300 mmol). The vial was sealed and the mixture shaken at room temperature overnight. The crude reaction mixture was further diluted with 2 mL of acetonitrile and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters Sunfire 5 μm C18 30×150 mm column at a gradient of 30-100% B and a flow rate of 30 mL/min. over 20 minutes with a 10 minute hold. Solvent was removed giving 18.5 mgs (41% yield) of 4-fluoro-2-(4-fluorophenyl)-5-(4-methoxy-2-methyl-5-(1-(oxazolo[4,5-c]pyridin-2-yl)cyclopropylcarbamoyl)phenyl)-N-methylbenzofuran-3-carboxamide as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.53 (m, 2 H), 1.80 (m, 2 H), 2.26 (s, 3 H), 2.87 (d, J=4.52 Hz, 3 H), 4.06 (s, 3 H), 7.12 (s, 1 H), 7.20 (m, 3 H), 7.43 (d, J=8.28 Hz, 1 H), 7.47 (d, J=5.52 Hz, 1 H), 7.68 (d, J=4.52 Hz, 1 H), 7.96 (s, 1 H), 8.09 (m, 2 H), 8.40 (d, J=5.52 Hz, 1 H), 8.71 (s, 1 H), 8.80 (d, 1 H). LCMS rt=2.405 min., m/z 609.3 (M+H), 97.2% purity. HPLC rt=6.878 min. (Sunfire C18), 100% purity and 10.719 min. (Gemini C18), 100% purity.

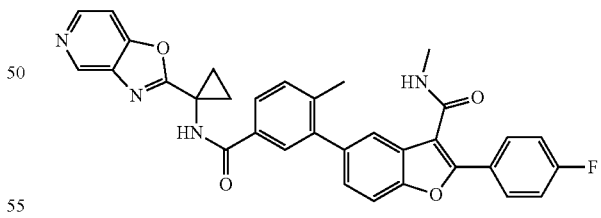

2-(4-fluorophenyl)-N-methyl-5-(2-methyl-5-(1-(oxazolo[4,5-d]pyridin-2-yl)cyclopropyl carbamoyl)phenyl)benzofuran-3-carboxamide. To a screw capped vial was added 3-(2-(4-fluorophenyl)-3-(methylcarbamoyl)benzofuran-5-yl)-4-methylbenzoic acid (40.3 mg, 0.1 mmol) in DMF (1.7 mL) along with N-ethyl-N,N-diisopropylpropan-2-amine (0.087 mL, 0.500 mmol), 1-(oxazolo[4,5-c]pyridin-2-yl)cyclopropanamine, 2 HCl (39.7 mg, 0.160 mmol) and finally HATU, 2-(3H-[1,2,3]triazolo[4,5-b]pyridin-3-yl)-1,1,3,3-tetramethylisouronium hexafluorophosphate(V) (152 mg, 0.400 mmol). The vial was capped and the mixture shaken over night at room temperature. The crude reaction mixture was further diluted with 2 mL of acetonitrile and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters Sunfire 5 μm C18 30×150 mm column at a gradient of 30-100% B and a flow rate of 30 mL/min. over 20 minutes with a 10 minute hold. Solvent was removed giving 29.5 mgs (52% yield) of 2-(4-fluorophenyl)-N-methyl-5-(2-methyl-5-(1-(oxazolo[4,5-c]pyridin-2-yl)cyclopropyl carbamoyl)phenyl)benzofuran-3-carboxamide as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.47-1.53 (m, 2H), 1.76-1.81 (m, 2 H), 2.31 (s, 3 H), 2.87-2.91 (m, 3 H), 7.20-7.27 (m, 2 H), 7.32 (dd, J=8.5, 1.8 Hz, 1 H), 7.37 (d, J=7.5 Hz, 1 H), 7.47 (dd, J=5.5, 1.0 Hz, 1 H), 7.51 (d, J=4.5 Hz, 1 H), 7.60 (d, J=8.3 Hz, 1 H), 7.70 (d, J=1.3 Hz, 1 H), 7.80-7.87 (m, 2 H), 8.08-8.16 (m, 2 H), 8.41 (d, J=5.5 Hz, 1 H), 8.74 (s, 1 H), 8.80 (s, 1 H). LCMS rt=2.472 min., m/z 561.3 (M+H). HPLC rt=6.888 min. (Sunfire C18), 99.0% purity and 10.934 min. (Gemini C18), 100% purity.

shaken over night at room temperature. The crude reaction mixture was further diluted with 2 mL of acetonitrile and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters Sunfire 5 μm C18 30×150 mm column at a gradient of 30-100% B and a flow rate of 30 mL/min. over 20 minutes with a 10 minute hold. Solvent was removed giving 25.7 mgs (44% yield) of 5-(3-fluoro-2-methyl-5-(1-(oxazolo[4,5-c]pyridin-2-yl)cyclopropylcarbamoyl)phenyl)-2-(4-fluorophenyl)-N-methylbenzofuran-3-carboxamide as a white solid. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.49-1.54 (m, 2 H), 1.76-1.83 (m, 2 H), 2.23 (d, J=2.5 Hz, 3 H), 2.89 (d, J=4.8 Hz, 3 H), 7.20-7.28 (m, 2 H), 7.33 (dd, J=8.5, 1.8 Hz, 1 H), 7.48 (dd, J=5.5, 1.0 Hz, 1 H), 7.51 (d, J=4.3 Hz, 1 H), 7.60-7.68 (m, 2 H), 7.71 (dd, J=12.4, 1.4 Hz, 2 H), 8.08-8.16 (m, 2 H), 8.41 (d, J=5.5 Hz, 1 H), 8.78-8.86 (m, 2 H). LCMS rt=2.572 min., m/z 579.2 (M+H). HPLC rt=7.168 min. (Sunfire C18), 97.4% purity and 11.323 min. (Gemini C18), 100% purity.

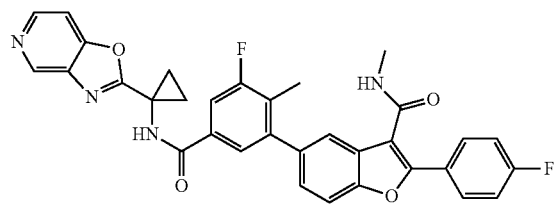 [SMILES: CNC(=O)c1c(-c2ccc(F)cc2)oc2ccc(-c3cc(C(=O)NC4(c5nc6cnccc6o5)CC4)cc(F)c3C)cc12]

5-(3-fluoro-2-methyl-5-(1-(oxazolo[4,5-c]pyridin-2-yl)cyclopropylcarbamoyl)phenyl)-2-(4-fluorophenyl)-N-methylbenzofuran-3-carboxamide. To a screw capped vial was added 3-fluoro-5-(2-(4-fluorophenyl)-3-(methylcarbamoyl)benzofuran-5-yl)-4-methylbenzoic acid (42.1 mg, 0.1 mmol) in DMF (1.7 mL) along with N-ethyl-N,N-diisopropylpropan-2-amine (0.087 mL, 0.500 mmol), 1-(oxazolo[4,5-c]pyridin-2-yl)cyclopropanamine, 2 HCl (39.7 mg, 0.160 mmol) and finally HATU, 2-(3H-[1,2,3]triazolo[4,5-b]pyridin-3-yl)-1,1,3,3-tetramethylisouronium hexafluorophosphate(V) (152 mg, 0.400 mmol). The vial was capped and the mixture

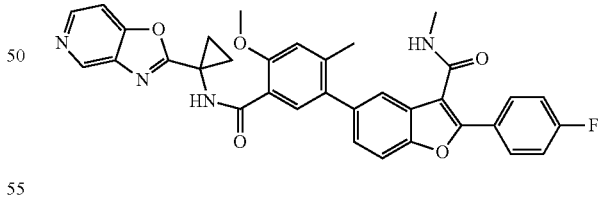

2-(4-fluorophenyl)-5-(4-methoxy-2-methyl-5-(1-(oxazolo[4,5-d]pyridin-2-yl)cyclopropyl carbamoyl)phenyl)-N-methylbenzofuran-3-carboxamide. To a screw capped vial was added 5-(2-(4-fluorophenyl)-3-(methylcarbamoyl)benzofuran-5-yl)-2-methoxy-4-methylbenzoic acid (43.3 mg, 0.1 mmol) in DMF (1.7 mL) along with N-ethyl-N,N-diisopropylpropan-2-amine (0.087 mL, 0.500 mmol), 1-(oxazolo[4,5-c]pyridin-2-yl)cyclopropanamine, 2 HCl (39.7 mg, 0.160 mmol) and finally HATU, 2-(3H-[1,2,3]triazolo[4,5-b]pyridin-3-yl)-1,1,3,3-tetramethylisouronium hexafluorophosphate(V) (152 mg, 0.400 mmol). The vial was capped and the mixture shaken overnight at room temperature. The crude reaction mixture was further diluted with 2 mL of acetonitrile and purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters Sunfire 5 µm C18 30×150 mm column at a gradient of 30-100% B and a flow rate of 30 mL/min. over 20 minutes with a 10 minute hold. Solvent was removed giving 18.7 mgs (31% yield) of 2-(4-fluorophenyl)-5-(4-methoxy-2-methyl-5-(1-(oxazolo[4,5-c]pyridin-2-yl)cyclopropylcarbamoyl)phenyl)-N-methylbenzofuran-3-carboxamide as a white solid. The LC/MS data was obtained on a Shimadzu analytical LC/Micromass Platform LC (ESI+) at 220 nm using the following set of conditions: Phenomenex Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 µm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.51-1.57 (m, 2 H), 1.77-1.83 (m, 2 H), 2.31 (s, 3 H), 2.88 (d, J=4.8 Hz, 3 H), 4.05 (s, 3 H), 7.09 (s, 1 H), 7.17-7.29 (m, 3 H), 7.48 (d, J=6.3 Hz, 1 H), 7.50-7.58 (m, 2 H), 7.62 (d, J=1.3 Hz, 1 H), 8.00 (s, 1 H), 8.09-8.18 (m, 2 H), 8.41 (d, J=5.5 Hz, 1 H), 8.74 (s, 1 H), 8.77-8.84 (m, 1 H). LCMS rt=2.543 min., m/z 591.3 (M+H). HPLC rt=7.158 min. (Sunfire C18), 97.9% purity and 11.306 min. (Gemini C18), 100% purity.

purified using a Shimadzu preparative HPLC employing acetonitrile/water/ammonium acetate where solvent A was 5% acetonitrile/95% water/10 mM ammonium acetate and solvent B was 5% water/95% acetonitrile/10 mM ammonium acetate with a Waters Sunfire 5 µm C18 30×150 mm column at a gradient of 30-100% B and a flow rate of 30 mL/min. over 20 minutes with a 10 minute hold. Solvent was removed giving 19.7 mgs (31.8% yield) of 4-fluoro-2-(4-fluorophenyl)-5-(4-methoxy-2-methyl-5-(1-(oxazolo[5,4-c]pyridin-2-yl)cyclopropylcarbamoyl)phenyl)-N-methylbenzofuran-3-carboxamide as a white solid. The LC/MS data was obtained on a Shimadzu analytical LC/Micromass Platform LC (ESI+) at 220 nm using the following set of conditions: Phenomenex Luna 3 µm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 µm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 µm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute. $^1$H NMR (400 MHz, THF-d8) δ ppm 1.13-1.20 (m, 2 H), 1.59-1.65 (m, 2 H), 2.25 (s, 3 H), 2.87 (d, J=4.5 Hz, 3 H), 4.02 (s, 3 H), 7.09 (s, 1 H), 7.16-7.28 (m, 3 H), 7.44 (d, J=8.5 Hz, 1 H), 7.76 (t, J=4.4 Hz, 1H), 7.87 (s, 1 H), 7.90 (d, J=5.3 Hz, 1 H), 7.99 (s, 1 H), 8.02-8.12 (m, 3 H), 8.51 (s, 1 H). LCMS rt=2.537 min., m/z 609.2 (M+H). HPLC rt=7.045 min. (Sunfire C18), 98.5% purity and 10.943 min. (Gemini C18), 97.8% purity.

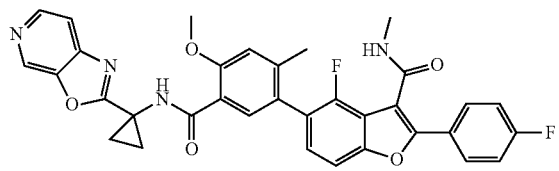 [SMILES: CNC(=O)c1c(-c2ccc(F)cc2)oc2ccc(-c3cc(C(=O)NC4(c5nc6ccncc6o5)CC4)c(OC)cc3C)c(F)c12]

4-fluoro-2-(4-fluorophenyl)-5-(4-methoxy-2-methyl-5-(1-(oxazolo[5,4-c]pyridin-2-yl)cyclopropyl carbamoyl)phenyl)-N-methylbenzofuran-3-carboxamide. To a screw capped vial was added 5-(4-fluoro-2-(4-fluorophenyl)-3-(methylcarbamoyl)benzofuran-5-yl)-2-methoxy-4-methylbenzoic acid (45.1 mg, 0.1 mmol) in DMF (1.7 mL) along with N-ethyl-N,N-diisopropylpropan-2-amine (0.087 mL, 0.500 mmol), freshly prepared 1-(oxazolo[5,4-c]pyridin-2-yl)cyclopropanamine, 2 HCl (0.040 g, 0.160 mmol) and finally HATU, 2-(3H-[1,2,3]triazolo[4,5-b]pyridin-3-yl)-1,1,3,3-tetramethylisouronium hexafluorophosphate(V) (152 mg, 0.400 mmol). The vial was capped and the mixture shaken over night at room temperature. The crude reaction mixture was further diluted with 2 mL of acetonitrile and

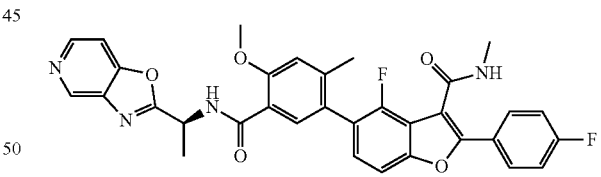

4-fluoro-2-(4-fluorophenyl)-5-(4-methoxy-2-methyl-5-((S)-1-(oxazolo[4,5-d]pyridin-2-yl)ethyl carbamoyl)phenyl)-N-methylbenzofuran-3-carboxamide. White solid, 24% yield. $^1$H NMR (400 MHz, THF-d8) δ ppm 1.73-1.82 (m, 3 H), 2.26 (s, 3 H), 2.87 (d, J=4.5 Hz, 3 H), 4.08 (s, 3 H), 5.59 (quin, J=7.1 Hz, 1 H), 7.12 (s, 1 H), 7.17-7.27 (m, 3 H), 7.44 (d, J=8.5 Hz, 1 H), 7.59 (d, J=5.5 Hz, 1 H), 7.74 (d, J=4.5 Hz, 1 H), 7.99 (s, 1 H), 8.07-8.15 (m, 2 H), 8.50 (d, J=5.5 Hz, 1 H), 8.73 (d, J=7.3 Hz, 1 H), 8.94 (s, 1 H). (Injection 1) LCMS rt=2.91 min., m/z 597.2 (M+H), m/z 595.3 (M−H). (Injection 2) LCMS rt=3.99 min., m/z 597.2 (M+H), m/z 595.3 (M−H). Injection 1 conditions: Column: Waters BEH C18, 2.0×50 mm, 1.7-µm; Mobile Phase A: 5:95 acetonitrile:water with 10 mM ammonium acetate; Mobile Phase B: 95:5 acetonitrile:water with 10 mM ammonium acetate; Temperature: 40° C.;

Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. HPLC rt=7.025 min. (Sunfire C18), 90.0% purity and 11.464 min. (Gemini C18), 91.3% purity. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

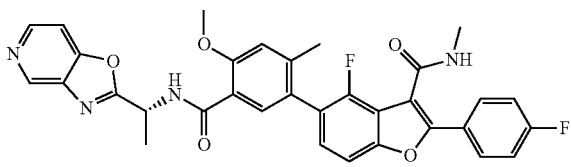 [SMILES: CNC(=O)c1c(-c2ccc(F)cc2)oc2ccc(-c3cc(C(=O)N[C@H](C)c4nc5cnccc5o4)c(OC)cc3C)c(F)c12]

4-fluoro-2-(4-fluorophenyl)-5-(4-methoxy-2-methyl-5-((R)-1-(oxazolo[4,5-d]pyridin-2-yl)ethyl carbamoyl)phenyl)-N-methylbenzofuran-3-carboxamide. White solid, 17% yield. $^1$H NMR (500 MHz, THF-d8) δ ppm 1.68 (s, 3H), 2.27 (s, 3H), 2.88 (d, J=4.58 Hz, 3 H), 4.09 (s, 3 H), 5.60 (q, J=7.10 Hz, 1 H), 7.13 (s, 1 H), 7.19-7.27 (m, 3 H), 7.46 (d, J=8.55 Hz, 1 H), 7.60 (dd, J=5.49, 0.92 Hz, 1 H), 7.75 (d, J=4.27 Hz, 1 H), 8.00 (s, 1 H), 8.08-8.15 (m, 2 H), 8.51 (d, J=5.49 Hz, 1 H), 8.74 (d, J=7.32 Hz, 1 H), 8.96 (s, 1 H). LCMS rt=2.422 min., m/z 597.3 (M+H). HPLC rt=6.965 min. (Sunfire C18), 95.4% purity and 11.344 min. (Gemini C18), 100% purity. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

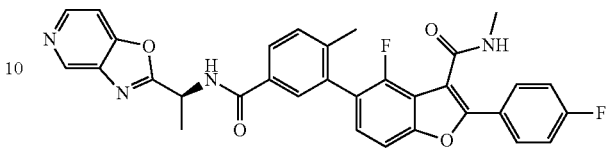

4-fluoro-2-(4-fluorophenyl)-N-methyl-5-(2-methyl-5-((S)-1-(oxazolo[4,5-d]pyridin-2-yl)ethyl carbamoyl)phenyl)benzofuran-3-carboxamide. White solid, 10% yield. $^1$H NMR (400 MHz, THF-d8) δ ppm 1.70 (s, 3 H), 2.23-2.27 (m, 3 H), 2.84-2.91 (m, 3 H), 5.64 (quin, J=7.28 Hz, 1 H), 7.18-7.28 (m, 3 H), 7.39 (d, J=8.03 Hz, 1 H), 7.47 (d, J=8.28 Hz, 1 H), 7.56 (dd, J=5.52, 1.00 Hz, 1 H), 7.72 (d, J=4.52 Hz, 1 H), 7.80 (d, J=1.76 Hz, 1 H), 7.87 (dd, J=8.03, 2.01 Hz, 1 H), 8.03-8.13 (m, 2 H), 8.33 (d, J=8.03 Hz, 1 H), 8.48 (d, J=5.52 Hz, 1 H), 8.91 (d, J=0.75 Hz, 1 H). (Injection 1) LCMS rt=2.78 min., m/z 567.2 (M+H), m/z 565.3 (M−H). (Injection 2) LCMS rt=3.89 min., m/z 567.2 (M+H), m/z 565.2 (M−H). Injection 1 conditions: Column: Waters BEH C18, 2.0×50 mm, 1.7 μm; Mobile Phase A: 5:95 acetonitrile:water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. HPLC rt=6.888 min. (Sunfire C18), 91.7% purity and 11.066 min. (Gemini C18), 99.2% purity. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

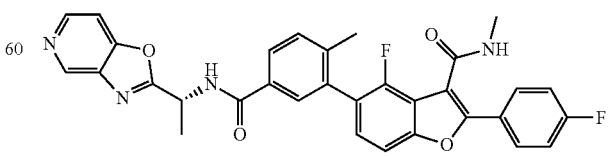

4-fluoro-2-(4-fluorophenyl)-N-methyl-5-(2-methyl-5-((R)-1-(oxazolo[4,5-d]pyridin-2-yl)ethyl carbamoyl)phenyl)

benzofuran-3-carboxamide. White solid, 15% yield. ¹H NMR (500 MHz, THF-d8) δ ppm 1.70 (s, 3 H), 2.24 (s, 3 H), 2.87 (d, J=4.58 Hz, 3 H), 5.64 (q, J=7.25 Hz, 1 H), 7.17-7.29 (m, 3 H), 7.38 (d, J=7.93 Hz, 1 H), 7.47 (d, J=8.24 Hz, 1 H), 7.56 (dd, J=5.49, 0.92 Hz, 1 H), 7.73 (d, J=4.58 Hz, 1 H), 7.80 (d, J=1.53 Hz, 1 H), 7.87 (dd, J=7.93, 1.83 Hz, 1 H), 8.00-8.11 (m, 2 H), 8.34 (d, J=7.93 Hz, 1 H), 8.47 (d, J=5.49 Hz, 1 H), 8.90 (s, 1 H). LCMS rt=2.327 min., m/z 567.3 (M+H). HPLC rt=6.738 min. (Sunfire C18), 94.0% purity and 11.113 min. (Gemini C18), 98.2% purity. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/ 0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/ methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

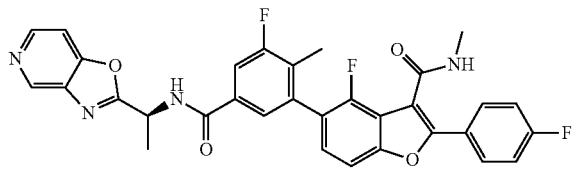 [SMILES: CNC(=O)c1c(-c2ccc(F)cc2)oc2ccc(-c3cc(C(=O)N[C@@H](C)c4nc5cnccc5o4)cc(F)c3C)c(F)c12]

4-fluoro-5-(3-fluoro-2-methyl-5-((S)-1-(oxazolo[4,5-d] pyridin-2-yl)ethylcarbamoyl)phenyl)-2-(4-fluorophenyl)-N-methylbenzofuran-3-carboxamide. White solid, 20% yield. ¹H NMR (400 MHz, THF-d8) δ ppm 1.70-1.73 (m, 3H), 2.17 (d, J=1.3 Hz, 3H), 2.87-2.90 (m, 3 H), 5.58-5.69 (m, 1 H), 7.21-7.30 (m, 3 H), 7.50 (d, J=8.5 Hz, 1H), 7.57 (d, J=5.5 Hz, 1H), 7.66-7.72 (m, 2 H), 7.75 (d, J=4.3 Hz, 1 H), 8.04-8.11 (m, 2 H), 8.42-8.51 (m, 2 H), 8.91 (s, 1 H). (Injection 1) LCMS rt=2.88 min., m/z 585.2 (M+H), m/z 583.2 (M−H). (Injection 2) LCMS rt=3.99 min., m/z 585.2 (M+H), m/z 583.3 (M−H). Injection 1 conditions: Column: Waters BEH C18, 2.0×50 mm, 1.7 μm; Mobile Phase A: 5:95 acetonitrile: water with 10 mM ammonium acetate; Mobile Phase B: 95:5 acetonitrile:water with 10 mM ammonium acetate; Temperature: 40° C.; Gradient: 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. HPLC rt=7.073 min. (Sunfire C18), 94.4% purity and 11.393 min. (Gemini C18), 96.4% purity. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/ methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

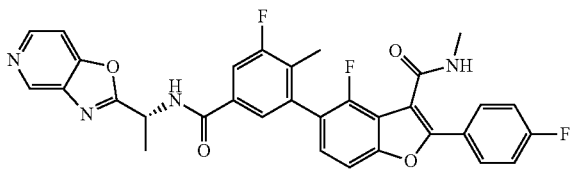 [SMILES: CNC(=O)c1c(-c2ccc(F)cc2)oc2ccc(-c3cc(C(=O)N[C@H](C)c4nc5cnccc5o4)cc(F)c3C)c(F)c12]

4-fluoro-5-(3-fluoro-2-methyl-5-((R)-1-(oxazolo[4,5-d] pyridin-2-yl)ethylcarbamoyl)phenyl)-2-(4-fluorophenyl)-N-methylbenzofuran-3-carboxamide. White solid, 27% yield. ¹H NMR (500 MHz, THF-d8) δ ppm 1.71 (s, 3 H), 2.16 (s, 3 H), 2.88 (d, J=4.58 Hz, 3 H), 5.63 (q, J=7.32 Hz, 1 H), 7.18-7.29 (m, 3 H), 7.48 (d, J=8.24 Hz, 1 H), 7.56 (dd, J=5.49, 0.61 Hz, 1 H), 7.65-7.73 (m, 2 H), 7.77 (d, J=4.58 Hz, 1 H), 8.02-8.10 (m, 2 H), 8.47 (d, J=5.49 Hz, 2 H), 8.90 (s, 1 H). LCMS rt=2.420 min., m/z 585.3 (M+H). HPLC rt=7.005 min. (Sunfire C18), 95.5% purity and 11.364 min. (Gemini C18), 97.6% purity. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/ 0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6×150 mm column employing water/ methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

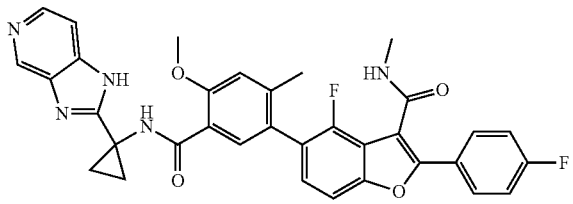 [SMILES: CNC(=O)c1c(-c2ccc(F)cc2)oc2ccc(-c3cc(C(=O)NC4(c5nc6cnccc6[nH]5)CC4)c(OC)cc3C)c(F)c12]

5-(5-(1-(1H-imidazo[4,5-c]pyridin-2-yl)cyclopropylcarbamoyl)-4-methoxy-2-methylphenyl)-4-fluoro-2-(4-fluorophenyl)-N-methylbenzofuran-3-carboxamide. To a screw cap vial was added 5-(4-fluoro-2-(4-fluorophenyl)-3-(methylcarbamoyl)benzofuran-5-yl) 2-methoxy-4-methylbenzoic acid (45.1 mg, 0.1 mmol) in DMF (1.8 mL) along with N-ethyl-N-isopropylpropan-2-amine (0.087 mL, 0.500 mmol), 1-(1H-imidazo[4,5-c]pyridin-2-yl)cyclopropanamine (26.1 mg, 0.150 mmol) and finally 2-(3H-[1,2,3]triazolo[4,5-b]pyridin-3-yl)-1,1,3,3-tetramethylisouronium hexafluorophosphate(V) (114 mg, 0.300 mmol). The vial was capped and shaken overnight at room temperature. The crude reaction mixture was further diluted with 2 mL of acetonitrile and purified using a Shimadzu preparative HPLC employing acetonitrile/water/trifluoroacetic acid where solvent A was 10% acetonitrile/90% water/0.1% trifluoroacetic acid and solvent B was 10% water/90% acetonitrile/0.1% trifluoroacetic acid with a Phenomenex-Luna 10 μm C18 30×100 mm column at a gradient of 30-100% B and a flow rate of 30 mL/min. over 10 minutes with a 15 minute hold. The desired material was free based (DCM/bicarb), dried over magnesium sulfate, decanted, and evaporated to dryness to give 30 mgs (48% yield) of 5-(5-(1-(1H-imidazo[4,5-c]pyridin-2-yl)cyclopropylcarbamoyl)-4-methoxy-2-methylphenyl)-4-fluoro-2-(4-fluorophenyl)-N-methylbenzofuran-3-carboxamide as a yellow solid. $^1$H NMR (500 MHz, CD$_3$OD) δ ppm 1.49-1.59 (m, 2 H), 1.76-1.85 (m, 2 H), 2.25 (br. s., 3 H), 2.90 (s, 3 H), 3.99-4.06 (m, 3 H), 7.13 (s, 1 H), 7.16-7.28 (m, 3 H), 7.38-7.52 (m, 2 H), 7.81-7.92 (m, 3 H), 8.20 (d, J=5.80 Hz, 1H), 8.69 (s, 1 H). LCMS rt=2.325 min., m/z 608.3 (M+H). HPLC rt=6.626 min. (Sunfire C18), 96.5% purity and 10.973 min. (Gemini C18), 99.5% purity. The LC/MS data was obtained on a Shimadzu analytical LC/Micromass Platform LC (ESI+) at 220 nm using the following set of conditions: Phenomenex Luna 3 μm C18, 2×50 mm column, with a gradient of 0-100% B (B=90% HPLC grade acetonitrile/0.1% trifluoroacetic acid/10% HPLC grade water), (A=90% HPLC grade water/0.1% trifluoroacetic acid/10% HPLC grade acetonitrile), in 4 minutes with a 1 minute hold at a rate of 0.8 mL/minute. HPLC purity was determined using a Shimadzu analytical LC at 254 nm and 256 nm with a Waters Sunfire C18 3.5 μm 4.6×150 mm column employing water/acetonitrile/0.1% trifluoroacetic acid with a gradient of 10-100% B (B=95% HPLC grade acetonitrile/0.1% trifluoroacetic acid/5% HPLC grade water), (A=95% HPLC grade water/0.1% trifluoroacetic acid/5% HPLC grade acetonitrile), in 10 minutes with a 10 minute hold at a rate of 1 mL/minute. The HPLC purity was then confirmed with an orthogonal solvent system and column using a Shimadzu analytical LC with a Phenomenex Gemini C18 3.0 μm 4.6× 150 mm column employing water/methanol/10 mM ammonium bicarbonate with a gradient of 10-100% B (B=95% HPLC grade methanol/10 mM ammonium bicarbonate/5% HPLC grade water), (A=95% HPLC grade water/10 mM ammonium bicarbonate/5% HPLC grade methanol), in 10 minutes with a 10 minute hold at a rate of 1 mL/minute.

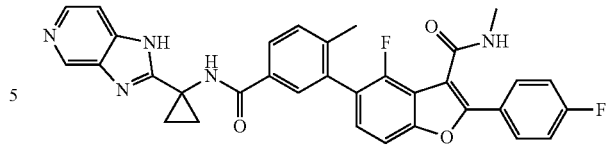

5-(5-(1-(1H-imidazo[4,5-o]pyridin-2-yl)cyclopropylcarbamoyl)-2-methylphenyl)-4-fluoro-2-(4-fluorophenyl)-N-methylbenzofuran-3-carboxamide. Yellow solid, 28% yield. $^1$H NMR (400 MHz, CD$_3$OD) δ ppm 1.50-1.58 (m, 2 H), 1.74-1.81 (m, 2 H), 2.24 (s, 3 H), 2.88-2.93 (m, 3 H), 7.19-7.30 (m, 3 H), 7.43 (d, J=8.03 Hz, 1 H), 7.46-7.53 (m, 2 H), 7.83 (d, J=2.01 Hz, 1 H), 7.86-7.98 (m, 5 H), 8.20 (d, J=5.77 Hz, 1 H), 8.68 (d, J=0.75 Hz, 1 H). (Injection 1) LCMS rt=2.96 min., m/z 578.2 (M+H), m/z 576.3 (M−H). (Injection 2) LCMS rt=3.80 min., m/z 578.2 (M+H), m/z 576.3 (M−H). Injection 1 conditions: Column: Waters BEH C18, 2.0×50 mm, 1.7 μm; Mobile Phase A: 5:95 acetonitrile:water with 10 mM ammonium acetate; Mobile Phase B: 95:5 acetonitrile:water with 10 mM ammonium acetate; Temperature: 40° C.; Gradient 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm; Mobile Phase A: 5:95 methanol:water with 10 mM ammonium acetate; Mobile Phase B: 95:5 methanol:water with 10 mM ammonium acetate; Temperature: 40° C.; Gradient 0.5 min hold at 0% B, 0-100% B over 4 minutes, then a 0.5-minute hold at 100% B; Flow: 0.5 mL/min. HPLC rt=6.435 min. (Sunfire C18), 94.5% purity and 10.733 min. (Gemini C18), 96.6% purity.

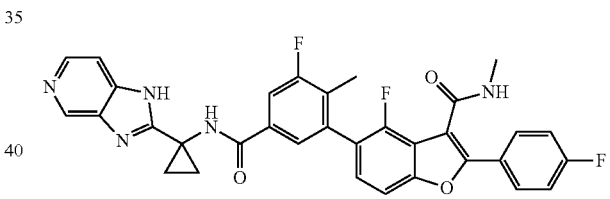

5-(5-(1-(1H-imidazo[4,5-c]pyridin-2-yl)cyclopropylcarbamoyl)-3-fluoro-2-methylphenyl)-4-fluoro-2-(4-fluorophenyl)-N-methylbenzofuran-3-carboxamide. Yellow solid, 35% yield. $^1$H NMR (400 MHz, CD$_3$OD) δ ppm 1.49-1.57 (m, 2 H), 1.73-1.82 (m, 2 H), 2.15 (s, 3 H), 2.90 (s, 3 H), 7.19-7.31 (m, 3 H), 7.45 (dd, J=5.77, 0.50 Hz, 1 H), 7.50 (d, J=8.53 Hz, 1 H), 7.66-7.72 (m, 2 H), 7.85-7.97 (m, 4 H), 8.18 (d, J=5.52 Hz, 1 H), 8.66 (d, J=0.50 Hz, 1 H). (Injection 1) LCMS rt=2.64 min., m/z 598.2 (M+H), m/z 596.2 (M−H). (Injection 2) LCMS rt=3.89 min., m/z 598.2 (M+H), m/z 596.2 (M−H). Injection 1 conditions: Column: Waters BEH C18, 2.0×50 mm, 1.7 μm; Mobile Phase A: 5:95 acetonitrile:water with 10 mM ammonium acetate; Mobile Phase B: 95:5 acetonitrile:water with 10 mM ammonium acetate; Temperature: 40° C.; Gradient 0.5 min hold at 0% B, 0-100% B over 4 minutes, then a 0.5-minute hold at 100% B; Flow: 1 mL/min. Injection 2 conditions: Column: Waters BEH C18, 2.0×50 mm, 1.7-μm; Mobile Phase A: 5:95 methanol:water with 10 mM ammonium acetate; Mobile Phase B: 95:5 methanol:water with 10 mM ammonium acetate; Temperature: 40° C.; Gradient: 0.5 min hold at 0% B, 0-100% B over 4 minutes, then a 0.5-minute hold at 100% B; Flow: 0.5 mL/min. HPLC rt=6.666 min. (Sunfire C18), 94.4% purity and 11.359 min. (Gemini C18), 95.1% purity.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

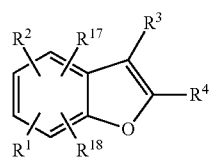

I where:
R$^1$ is phenyl substituted with 1 CON(R$^5$)(R$^6$); and where said phenyl is also substituted with 0-2 substituents selected from the group consisting of halo, cyano, alkyl, haloalkyl, hydroxyalkyl, alkoxyalkyl, (carboxy)alkyl, alkoxy, hydroxyalkyloxy, alkoxyalkyloxy, benzyloxy, (CON(R$^7$)(R$^8$))alkyloxy, tetrahydropyranyloxy, carboxy, alkoxycarbonyl, alkylsulfonyl, (carboxy)alkenyl, (alkoxycarbonyl)alkenyl, alkylcarboxamido, alkoxycarboxamido, alkylsulfamido, (alkylsulfamido)alkyl, Ar$^2$, and SO$_2$N(R$^7$)(R$^8$); and where said phenyl is also substituted with 0-2 substituents selected from the group consisting of halo; nitro; alkyl; cycloalkyl; haloalkyl; aminoalkyl; hydroxyalkyl; alkoxyalkyl; hydroxy; alkoxy; O(R$^9$); cycloalkoxy; amino; alkylamino; dialkylamino; alkylcarboxamido; alkoxycarboxamido; alkoxyalkylcarboxamido; furanyl, thienyl, pyrazolyl substituted with 0-2 alkyl substituents; pyridinyl substituted with 0-2 halo, cyano, alkyl, hydroxy, alkoxy, amino, or alkylaminocarbonyl substituents; pyrimidinyl; pyrimidinedionyl; aminopyrimidinyl; indolyl; isoquinolinyl; and phenyl substituted with 0-2 substituents selected from the group consisting of halo, alkyl, cyanoalkyl, hydroxyalkyl, alkoxyalkyl, hydroxy, alkoxy, amino, carboxy, alkoxycarbonyl, aminocarbonyl, alkylaminocarbonyl, dialkylaminocarbonyl, alkylcarboxamido, carboxyalkenyl, and phenyl;
R$^2$ is hydrogen, halo, nitro, amino, phenyl, or (R$^{10}$)(R$^{11}$)N;
R$^3$ is cyano, alkoxycarbonyl, (cycloalkyl)oxycarbonyl, (alkylsulfonyl)aminocarbonyl, CON(R$^{12}$)(R$^{13}$), (R$^{12}$)(R$^{13}$)NCONH, triazolyl, thiazolyl, or tetrazolyl;
R$^4$ is phenyl substituted with 0-2 halo, alkoxy, phenoxy, or halophenoxy substituents;
R$^5$ is

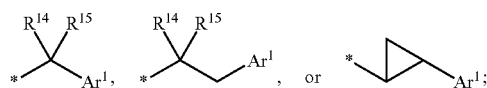

R$^6$ is hydrogen, alkyl, hydroxyalkyl, or alkoxyalkyl;
R$^7$ is hydrogen, alkyl, hydroxyalkyl, cycloalkyl, or benzyl;
R$^8$ is hydrogen or alkyl;

or R$^7$ and R$^8$ taken together with the nitrogen to which they are attached is azetidinyl, pyrrolidinyl, piperidinyl, piperazinyl, or morpholinyl;
R$^9$ is haloalkyl, cyanoalkyl, (cycloalkyl)alkyl, hydroxyalkyl, alkoxyalkyl aminoalkyl, (R$^{16}$)alkyl, (Ar$^3$)alkyl, alkynyl, or aminocycloalkyl;
R$^{10}$ is hydrogen, alkyl, or alkylsulfonyl;
R$^{11}$ is hydrogen, alkyl, hydroxyalkyl, alkoxyalkyl, or alkylsulfonyl;
R$^{12}$ is hydrogen, alkyl, or cycloalkyl;
R$^{13}$ is hydrogen, alkyl, or cycloalkyl;
or R$^{12}$ and R$^{13}$ taken together with the nitrogen to which they are attached is azetidinyl, pyrrolidinyl, piperidinyl, piperazinyl, or morpholinyl;
R$^{14}$ is hydrogen, alkyl, hydroxyalkyl, or alkoxyalkyl;
R$^{15}$ is hydrogen, alkyl, hydroxyalkyl, or alkoxyalkyl;
or R$^{14}$ and R$^{15}$ taken together is ethylene, propylene, butylene, pentylene, or hexylene;
R$^{16}$ is CONH$_2$, H$_2$NCONH, dibenzylamino, phthalimido, amino, alkylamino, dialkylamino, azetidinyl, pyrrolidinyl, piperidinyl, piperazinyl, morpholinyl where azetidinyl, pyrrolidinyl, piperidinyl, piperazinyl, or morpholinyl is substituted with 0-3 alkyl or alkoxycarbonyl substituents;
R$^{17}$ is hydrogen, halo, alkyl, or alkoxy;
R$^{18}$ is hydrogen, halo, alkyl, or alkoxy;
Ar$^1$ is azaindolyl, benzimidazolyl, azabenzimidazolyl, benzoxazolyl, oxazolopyridinyl, imidazopyridinyl, quinazolinyl, pyridopyrimidinyl or naphthyridinyl, and is substituted with 0-2 substituents selected from halo, alkyl, cycloalkyl, haloalkyl, alkoxyalkyl, hydroxy, alkoxy, amino, alkylamino, dialkylamino, aminocarbonyl, pyridinyl, phenyl, halophenyl, alkylphenyl, and alkoxyphenyl;
Ar$^2$ is phenyl, biphenyl, or pyridinyl and is substituted with 0-2 substituents selected from halo, alkyl, cyano, hydroxy, alkoxy, and carboxy; and
Ar$^3$ is furanyl, thienyl, pyrrolyl, pyrazolyl, isoxazolyl, isothiazolyl, imidazolyl, oxadiazolyl, thiadiazolyl, triazolyl, pyridinyl, indolyl, or phenyl and is substituted with 0-2 substituents selected from halo, alkyl, haloalkyl, hydroxyl, and alkoxy;
or a pharmaceutically acceptable salt thereof.
2. A compound of claim 1 where R$^2$ is hydrogen or halo, R$^{17}$ is hydrogen, and R$^{18}$ is hydrogen.
3. A compound of claim 2 where
R$^1$ is phenyl substituted with 1 CON(R$^5$)(R$^6$) and 0-2 halo, alkyl, alkoxy, or (CON(R$^7$)(R$^8$))alkyloxy substituents;
R$^2$ is hydrogen or halo;
R$^3$ is CON(R$^{12}$)(R$^{13}$);
R$^4$ is phenyl substituted with 0-2 halo substituents;
R$^5$ is

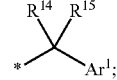

R$^6$ is hydrogen;
R$^7$ is hydrogen or alkyl;
R$^8$ is hydrogen or alkyl;
R$^{12}$ is hydrogen or alkyl;
R$^{13}$ is hydrogen or alkyl;
R$^{14}$ is hydrogen or alkyl;
R$^{15}$ is hydrogen or alkyl;
or R$^{14}$ and R$^{15}$ taken together is ethylene; and Ar¹ is azaindolyl, benzimidazolyl, azabenzimidazolyl, benzoxazolyl, oxazolopyridinyl, imidazopyridinyl, quinazolinyl, pyridopyrimidinyl or naphthyridinyl; or a pharmaceutically acceptable salt thereof.

4. A compound of claim 3 where R¹ is phenyl substituted with 1 CON(R⁵)(R⁶) and 1-2 fluoro, methyl, methoxy, or (CONH₂)CH₂O substituents; R² is hydrogen or fluoro; R³ is CON(R¹²)(R¹³); R⁴ is phenyl substituted with 1 fluoro substituent; R⁵ is

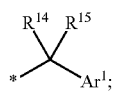

R⁶ is hydrogen; R¹² is methyl; R¹³ is hydrogen; R¹⁴ is methyl, R¹⁵ is hydrogen; or R¹⁴ and R¹⁵ taken together is ethylene; and Ar¹ is azaindolyl, benzimidazolyl, azabenzimidazolyl, benzoxazolyl, oxazolopyridinyl, imidazopyridinyl, quinazolinyl, pyridopyrimidinyl or naphthyridinyl; or a pharmaceutically acceptable salt thereof.

5. A compound of claim 4 where R¹ is phenyl substituted with 1 CON(R⁵)(R⁶) and 1-2 fluoro, methyl, or methoxy substituents; R² is hydrogen or fluoro; R³ is CON(R¹²)(R¹³); R⁴ is 4-fluorophenyl; R⁵ is

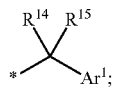

R⁶ is hydrogen; R¹² is methyl; R¹³ is hydrogen; R¹⁴ and R¹⁵ taken together is ethylene; and Ar¹ is azaindolyl, benzimidazolyl, azabenzimidazolyl, benzoxazolyl, oxazolopyridinyl, imidazopyridinyl, quinazolinyl, pyridopyrimidinyl or naphthyridinyl; or a pharmaceutically acceptable salt thereof.

6. A compound of claim 1 where R¹ is phenyl substituted with 1 CON(R⁵)(R⁶) substituent and also substituted with 0-2 halo, alkyl, or alkoxy substituents.

7. A compound of claim 6 where R⁵ is

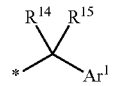

and R¹⁴ and R¹⁵ taken together is ethylene.

8. A compound of claim 1 where Ar¹ is azaindolyl, benzimidazolyl, azabenzimidazolyl, benzoxazolyl, oxazolopyridinyl, imidazopyridinyl, quinazolinyl, pyridopyrimidinyl or naphthyridinyl, and is substituted with 0-2 substituents selected from halo, alkyl, cycloalkyl, haloalkyl, alkoxyalkyl, hydroxy, alkoxy, amino, alkylamino, dialkylamino, aminocarbonyl, pyridinyl, phenyl, halophenyl, alkylphenyl, and alkoxyphenyl.

9. A compound of claim 1 where Ar¹ is azaindolyl, benzimidazolyl, azabenzimidazolyl, benzoxazolyl, oxazolopyridinyl, imidazopyridinyl, quinazolinyl, pyridopyrimidinyl or naphthyridinyl.

10. A compound of claim 1 where R¹ is phenyl substituted with 1 CON(R⁵)(R⁶); and where said phenyl is also substituted with 0-2 substituents selected from the group consisting of halo, cyano, alkyl, haloalkyl, hydroxyalkyl, alkoxyalkyl, (carboxy)alkyl, alkoxy, hydroxyalkyloxy, alkoxyalkyloxy, benzyloxy, (CON(R⁷)(R⁸))alkyloxy, tetrahydropyranyloxy, carboxy, alkoxycarbonyl, alkylsulfonyl, (carboxy)alkenyl, (alkoxycarbonyl)alkenyl, alkylcarboxamido, alkoxycarboxamido, alkylsulfamido, (alkylsulfamido)alkyl, Ar², and SO₂N(R⁷)(R⁸); and where said phenyl is also substituted with 0-2 substituents selected from the group consisting of halo; nitro; alkyl; cycloalkyl; haloalkyl; aminoalkyl; hydroxyalkyl; alkoxyalkyl; hydroxy; alkoxy; O(R⁹); cycloalkoxy; amino; alkylamino; dialkylamino; alkylcarboxamido; alkoxycarboxamido; alkoxyalkylcarboxamido; furanyl, thienyl, pyrazolyl substituted with 0-2 alkyl substituents; pyridinyl substituted with 0-2 halo, cyano, alkyl, hydroxy, alkoxy, amino, or alkylaminocarbonyl substituents; pyrimidinyl; pyrimidinedionyl; aminopyrimidinyl; indolyl; isoquinolinyl; and phenyl substituted with 0-2 substituents selected from the group consisting of halo, alkyl, cyanoalkyl, hydroxyalkyl, alkoxyalkyl, hydroxy, alkoxy, amino, carboxy, alkoxycarbonyl, aminocarbonyl, alkylaminocarbonyl, dialkylaminocarbonyl, alkylcarboxamido, carboxyalkenyl, and phenyl;

R² is hydrogen, halo, or (R¹⁰)(R¹¹)N;

R³ is cyano, alkoxycarbonyl, (cycloalkyl)oxycarbonyl, (alkylsulfonyl)aminocarbonyl, CON(R¹²)(R¹³), (R¹²)(R¹³)NCONH, triazolyl, thiazolyl, or tetrazolyl;

R⁴ is phenyl substituted with 0-2 halo, alkoxy, phenoxy, or halophenoxy substituents;

R⁵ is

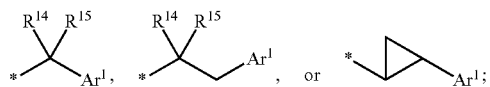

R⁶ is hydrogen, alkyl, hydroxyalkyl, or alkoxyalkyl;

R⁷ is hydrogen, alkyl, hydroxyalkyl, cycloalkyl, or benzyl;

R⁸ is hydrogen or alkyl;

or R⁷ and R⁸ taken together with the nitrogen to which they are attached is azetidinyl, pyrrolidinyl, piperidinyl, piperazinyl, or morpholinyl;

R⁹ is haloalkyl, cyanoalkyl, (cycloalkyl)alkyl, hydroxyalkyl, alkoxyalkyl, aminoalkyl, (R¹⁶)alkyl, (Ar³)alkyl, alkynyl, or aminocycloalkyl;

R¹⁰ is alkylsulfonyl;

R¹¹ is hydrogen, alkyl, hydroxyalkyl, or alkoxyalkyl;

R¹² is hydrogen, alkyl, or cycloalkyl;

R¹³ is hydrogen, alkyl, or cycloalkyl;

or R¹² and R¹³ taken together with the nitrogen to which they are attached is azetidinyl, pyrrolidinyl, piperidinyl, piperazinyl, or morpholinyl;

R¹⁴ is hydrogen, alkyl, hydroxyalkyl, or alkoxyalkyl;

R¹⁵ is hydrogen, alkyl, hydroxyalkyl, or alkoxyalkyl;

or R¹⁴ and R¹⁵ taken together is ethylene, propylene, butylene, pentylene, or hexylene;

R¹⁶ is CONH₂, H₂NCONH, dibenzylamino, phthalimido, amino, alkylamino, dialkylamino, azetidinyl, pyrrolidinyl, piperidinyl, piperazinyl, morpholinyl where azetidinyl, pyrrolidinyl, piperidinyl, piperazinyl, or morpholinyl is substituted with 0-3 alkyl or alkoxycarbonyl substituents;

R¹⁷ is hydrogen, fluoro, or chloro;

R¹⁸ is hydrogen, fluoro, or chloro;

Ar¹ is azaindolyl, benzimidazolyl, azabenzimidazolyl, benzoxazolyl, oxazolopyridinyl, imidazopyridinyl, quinazolinyl, pyridopyrimidinyl or naphthyridinyl, and is substituted with 0-2 substituents selected from halo, alkyl, cycloalkyl, haloalkyl, alkoxyalkyl, hydroxy, alkoxy, amino, alkylamino, dialkylamino, aminocarbonyl, pyridinyl, phenyl, halophenyl, alkylphenyl, and alkoxyphenyl;

$Ar^2$ is phenyl, biphenyl, or pyridinyl and is substituted with 0-2 substituents selected from halo, alkyl, cyano, hydroxy, alkoxy, and carboxy; and $Ar^3$ is furanyl, thienyl, pyrrolyl, pyrazolyl, isoxazolyl, isothiazolyl, imidazolyl, oxadiazolyl, thiadiazolyl, triazolyl, pyridinyl, indolyl, or phenyl and is substituted with 0-2 substituents selected from halo, alkyl, haloalkyl, hydroxyl, and alkoxy;

or a pharmaceutically acceptable salt thereof.

11. A compound of claim 10 where $R^{17}$ and $R^{18}$ are hydrogen.

12. A compound of claim 1 selected from the group consisting of 5-(5-(1-(1,8-naphthyridin-2-yl)cyclopropylcarbamoyl)-2-methylphenyl)-2-(4-fluorophenyl)-N -methylbenzofuran-3-carboxamide;

5-(5-(1-(1,7-naphthyridin-2-yl)cyclopropylcarbamoyl)-2-methylphenyl)-2-(4-fluorophenyl)-N -methylbenzofuran-3-carboxamide;

5-(5-(1-(1,8-naphthyridin-2-yl)cyclopropylcarbamoyl)-2-methylphenyl)-4-fluoro-2-(4-fluoro phenyl)-N-methyl-benzofuran-3-carboxamid;

5-(5-(1-(1H-pyrrolo[3,2-c]pyridin-4-yl)cyclopropylcarbamoyl)-2-methylphenyl)-4-fluoro-2-(4-fluorophenyl)-N-methylbenzofuran-3-carboxamide;

5-(5-(1-(1H-pyrrolo[3,2-b]pyridin-5-yl)cyclopropylcarbamoyl)-2-methylphenyl)-4-fluoro-2-(4-fluorophenyl)-N-methylbenzofuran-3-carboxamide;

5-(5-(1-(1,6-naphthyridin-2-yl)cyclopropylcarbamoyl)-2-methylphenyl)-2-(4-fluorophenyl)-N -methylbenzofuran-3-carboxamide;

5-(5-(1-(1,5-naphthyridin-2-yl)cyclopropylcarbamoyl)-2-methylphenyl)-2-(4-fluorophenyl)-N -methylbenzofuran-3-carboxamide;

5-(5-(1-(1,7-naphthyridin-2-yl)cyclopropylcarbamoyl)-2-methylphenyl)-4-fluoro-2-(4-fluoro phenyl)-N-methyl-benzofuran-3-carboxamide;

5-(5-(1-(1,6-naphthyridin-2-yl)cyclopropylcarbamoyl)-2-methylphenyl)-4-fluoro-2-(4-fluoro phenyl)-N-methyl-benzofuran-3-carboxamide;

5-(5-(1-(1,5-naphthyridin-2-yl)cyclopropylcarbamoyl)-2-methylphenyl)-4-fluoro-2-(4-fluoro phenyl)-N-methyl-benzofuran-3-carboxamide;

5-(5-(1-(1,8-naphthyridin-2-yl)cyclopropylcarbamoyl)-3-fluoro-2-methylphenyl)-4-fluoro-2-(4-fluorophenyl)-N-methylbenzofuran-3-carboxamide;

5-(5-(1-(1,7-naphthyridin-2-yl)cyclopropylcarbamoyl)-3-fluoro-2-methylphenyl)-4-fluoro-2-(4-fluorophenyl)-N-methylbenzofuran-3-carboxamide 5-(5-(1-(1,6-naphthyridin-2-yl)cyclopropylcarbamoyl)-3-fluoro-2-methylphenyl)-4-fluoro-2-(4-fluorophenyl)-N-methylbenzofuran-3-carboxamide;

5-(5-(1-(1,5-naphthyridin-2-yl)cyclopropylcarbamoyl)-3-fluoro-2-methylphenyl)-4-fluoro-2-(4-fluorophenyl)-N-methylbenzofuran-3-carboxamide;

5-(5-(1-(1,6-naphthyridin-2-yl)cyclopropylcarbamoyl)-4-methoxy-2-methylphenyl)-4-fluoro-2-(4-fluorophenyl)-N-methylbenzofuran-3-carboxamide;

5-(5-(1-(1,7-naphthyridin-2-yl)cyclopropylcarbamoyl)-4-methoxy-2-methylphenyl)-4-fluoro-2-(4-fluorophenyl)-N-methylbenzofuran-3-carboxamide;

5-(5-(1-(1,7-naphthyridin-2-yl)cyclopropylcarbamoyl)-2-(2-amino-2-oxoethoxy)-4-methoxy phenyl)-2-(4-fluorophenyl)-N-methylbenzofuran-3-carboxamide;

4-fluoro-2-(4-fluorophenyl)-N-methyl-5-(2-methyl-5-(1-(pyrido[4,3-d]pyrimidin-2-yl)cyclo -propylcarbamoyl)phenyl)benzofuran-3-carboxamide;

4-fluoro-2-(4-fluorophenyl)-N-methyl-5-(2-methyl-5-(1-(pyrido[3,4-d]pyrimidin-2-yl)cyclopropyl carbamoyl)phenyl)benzofuran-3-carboxamide;

4-fluoro-2-(4-fluorophenyl)-N-methyl-5-(2-methyl-5-(1-(oxazolo[4,5-c]pyridin-2-yl)cyclopropyl carbamoyl)phenyl)benzofuran-3-carboxamide;

4-fluoro-5-(3-fluoro-2-methyl-5-(1-(oxazolo[4,5-c]pyridin-2-yl)cyclopropylcarbamoyl)phenyl)-2-(4-fluorophenyl)-N-methylbenzofuran-3-carboxamide;

4-fluoro-2-(4-fluorophenyl)-5-(4-methoxy-2-methyl-5-(1-(oxazolo[4,5-c]pyridin-2-yl)cyclopropyl carbamoyl)phenyl)-N-methylbenzofuran-3-carboxamide;

2-(4-fluorophenyl)-N-methyl-5-(2-methyl-5-(1-(oxazolo[4,5-c]pyridin-2-yl)cyclopropyl carbamoyl)phenyl)benzofuran-3-carboxamide;

5-(3-fluoro-2-methyl-5-(1-(oxazolo[4,5-c]pyridin-2-yl)cyclopropylcarbamoyl)phenyl)-2-(4-fluorophenyl)-N-methylbenzofuran-3-carboxamide;

2-(4-fluorophenyl)-5-(4-methoxy-2-methyl-5-(1-(oxazolo[4,5-c]pyridin-2-yl)cyclopropyl carbamoyl)phenyl)-N-methylbenzofuran-3-carboxamide;

4-fluoro-2-(4-fluorophenyl)-5-(4-methoxy-2-methyl-5-(1-(oxazolo[5,4-c]pyridin-2-yl)cyclopropyl carbamoyl)phenyl)-N-methylbenzofuran-3-carboxamide;

4-fluoro-2-(4-fluorophenyl)-5-(4-methoxy-2-methyl-5-((S)-1-(oxazolo[4,5-c]pyridin-2-yl)ethyl carbamoyl)phenyl)-N-methylbenzofuran-3-carboxamide;

4-fluoro-2-(4-fluorophenyl)-5-(4-methoxy-2-methyl-5-((R)-1-(oxazolo[4,5-c]pyridin-2-yl)ethyl carbamoyl)phenyl)-N-methylbenzofuran-3-carboxamide;

4-fluoro-2-(4-fluorophenyl)-N-methyl-5-(2-methyl-5-((S)-1-(oxazolo[4,5-c]pyridin-2-yl)ethyl carbamoyl)phenyl)benzofuran-3-carboxamide;

4-fluoro-2-(4-fluorophenyl)-N-methyl-5-(2-methyl-5-(((R) -1-(oxazolo[4,5-c]pyridin-2-yl)ethyl carbamoyl)phenyl)benzofuran-3-carboxamide;

4-fluoro-5-(3-fluoro-2-methyl-5-((S)-1-(oxazolo[4,5-c]pyridin-2-yl)ethyl carbamoyl)phenyl)-2-(4-fluorophenyl)-N-methylbenzofuran-3-carboxamide;

4-fluoro-5-(3-fluoro-2-methyl-5-((R)-1-(oxazolo[4,5-c]pyridin-2-yl)ethyl carbamoyl)phenyl)-2-(4-fluorophenyl)-N-methylbenzofuran-3-carboxamide;

5-(5-(1-(1H-imidazo[4,5-c]pyridin-2-yl)cyclopropylcarbamoyl)-4-methoxy-2-methylphenyl)-4-fluoro-2-(4-fluorophenyl)-N-methylbenzofuran-3-carboxamide;

5-(5-(1-(1H-imidazo[4,5-c]pyridin-2-yl)cyclopropylcarbamoyl)-2-methylphenyl)-4-fluoro-2-(4-fluorophenyl)-N-methylbenzofuran-3-carboxamide; and 5-(5-(1-(1H-imidazo[4,5-c]pyridin-2-yl)cyclopropylcarbamoyl)-3-fluoro-2-methylphenyl)-4-fluoro-2-(4-fluorophenyl)-N-methylbenzofuran-3-carboxamide;

or a pharmaceutically acceptable salt thereof.

13. A composition comprising a compound of claim 1 or a pharmaceutically acceptable salt thereof and a pharmaceutically acceptable carrier.

14. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 8,354,410 B2
APPLICATION NO. : 13/043747
DATED : January 15, 2013
INVENTOR(S) : Kap-Sun Yeung et al.

It is certified that error appears in the above-identified patent and that said Letters Patent is hereby corrected as shown below:

On the Title Page:

Item (73), Assignee, change "Bristol-Meyers Squibb Company" to -- Bristol-Myers Squibb Company --.

In the Claims:

Claim 1:

Column 64, line 5, change "alkoxyalkyl" to -- alkoxyalkyl, --.

Claim 12:

Column 67, lines 19 and 20, change "N -methylbenzofuran" to -- N-methylbenzofuran --.
Column 67, lines 22 and 23, change "N -methylbenzofuran" to -- N-methylbenzofuran --.
Column 67, line 25, change "(4-fluoro phenyl)" to -- (4-fluorophenyl) --.
Column 67, line 26, change "3-carboxamid;" to -- 3-carboxamide; --.
Column 67, lines 34 and 35, change "N -methylbenzofuran" to -- N-methylbenzofuran --.
Column 67, lines 37 and 38, change "N -methylbenzofuran" to -- N-methylbenzofuran --.
Column 67, line 40, change "(4-fluoro phenyl)" to -- (4-fluorophenyl) --.
Column 67, line 43, change "(4-fluoro phenyl)" to -- (4-fluorophenyl) --.
Column 67, line 46, change "(4-fluoro phenyl)" to -- (4-fluorophenyl) --.
Column 67, line 53, change "3-carboxamide" to -- 3-carboxamide; --.
Column 68, line 2, change "methoxy phenyl)" to -- methoxyphenyl) --.
Column 68, line 5, change "cyclo -propylcarbamoyl)" to -- cyclopropylcarbamoyl) --.
Column 68, line 8, change "cyclopropyl carbamoyl)" to -- cyclopropylcarbamoyl) --.
Column 68, line 11, change "cyclopropyl carbamoyl)" to -- cyclopropylcarbamoyl) --.

Signed and Sealed this
Twenty-ninth Day of April, 2014

Michelle K. Lee
*Deputy Director of the United States Patent and Trademark Office*

CERTIFICATE OF CORRECTION (continued)
U.S. Pat. No. 8,354,410 B2

In the Claims:

Claim 12:

Column 68, line 17, change "cyclopropyl carbamoyl)" to -- cyclopropylcarbamoyl) --.

Column 68, line 20, change "cyclopropyl carbamoyl)" to -- cyclopropylcarbamoyl) --.

Column 68, line 26, change "cyclopropyl carbamoyl)" to -- cyclopropylcarbamoyl) --.

Column 68, line 29, change "cyclopropyl carbamoyl)" to -- cyclopropylcarbamoyl) --.

Column 68, line 32, change "ethyl carbamoyl)" to -- ethylcarbamoyl) --.

Column 68, line 35, change "ethyl carbamoyl)" to -- ethylcarbamoyl) --.

Column 68, line 38, change "ethyl carbamoyl)" to -- ethylcarbamoyl) --.

Column 68, line 41, change "(((R) -1-" to -- ((R)-1- --.

Column 68, line 41, change "ethyl carbamoyl)" to -- ethylcarbamoyl) --.

Column 68, line 44, change "ethyl carbamoyl)" to -- ethylcarbamoyl) --.

Column 68, line 47, change "ethyl carbamoyl)" to -- ethylcarbamoyl) --.